US009642615B2

(12) United States Patent
Halac et al.

(10) Patent No.: US 9,642,615 B2
(45) Date of Patent: May 9, 2017

(54) SUTURE LOCKING DEVICE AND METHODS

(75) Inventors: Jason M. Halac, Solana Beach, CA (US); James A. McCrea, Burlingame, CA (US); Troy T. White, Maple Grove, MN (US); Bernhard Kaeferlein, Champlin, MN (US); Ali Hassan, Palo Alto, CA (US); Zihan Lin, Irvine, CA (US)

(73) Assignee: ST. JUDE MEDICAL PUERTO RICO LLC, Caguas (FR)

( * ) Notice: Subject to any disclaimer, the term of this patent is extended or adjusted under 35 U.S.C. 154(b) by 354 days.

(21) Appl. No.: 13/442,517

(22) Filed: Apr. 9, 2012
(Under 37 CFR 1.47)

(65) Prior Publication Data

US 2013/0072949 A1 Mar. 21, 2013

Related U.S. Application Data

(60) Provisional application No. 61/474,223, filed on Apr. 11, 2011.

(51) Int. Cl.
*A61B 17/04* (2006.01)

(52) U.S. Cl.
CPC ...... *A61B 17/0487* (2013.01); *A61B 17/0467* (2013.01); *A61B 2017/0488* (2013.01)

(58) Field of Classification Search
CPC ............ A61B 17/0467; A61B 17/0487; A61B 2017/0488; A61B 2017/049; A61B 17/0485
USPC .................................... 606/1, 139–148, 232
See application file for complete search history.

(56) References Cited

U.S. PATENT DOCUMENTS

| 5,643,292 | A | 7/1997 | Hart | |
|---|---|---|---|---|
| 6,059,800 | A | 5/2000 | Hart et al. | |
| 6,200,329 | B1 * | 3/2001 | Fung et al. | 606/232 |
| 6,254,620 | B1 * | 7/2001 | Koh et al. | 606/167 |
| 6,524,328 | B2 * | 2/2003 | Levinson | 606/232 |
| 7,094,246 | B2 * | 8/2006 | Anderson et al. | 606/148 |
| 7,918,867 | B2 | 4/2011 | Dana et al. | |
| 8,105,355 | B2 * | 1/2012 | Page et al. | 606/232 |
| 2007/0093858 | A1 | 4/2007 | Gambale et al. | |
| 2007/0270908 | A1 | 11/2007 | Stokes et al. | |
| 2010/0049213 | A1 * | 2/2010 | Serina et al. | 606/139 |

FOREIGN PATENT DOCUMENTS

| FR | 2682867 A1 | 4/1993 |
|---|---|---|
| WO | 2009052438 A2 | 4/2009 |

OTHER PUBLICATIONS

International Search Report and Written Opinion, PCT/US2012/032676, Feb. 18, 2013 (18 pp.).

\* cited by examiner

*Primary Examiner* — Christopher L Templeton
*Assistant Examiner* — Lucas Paez
(74) *Attorney, Agent, or Firm* — Holland & Hart

(57) ABSTRACT

A suture locking device includes a suture locking assembly, a suture cutting member, and an actuator assembly. The actuator assembly includes a first actuator operable longitudinally to lock the suture with the suture locking assembly, and a second actuator operable laterally to concurrently cut the suture with the suture cutting member and disconnect the suture locking assembly from the suture locking device.

21 Claims, 23 Drawing Sheets

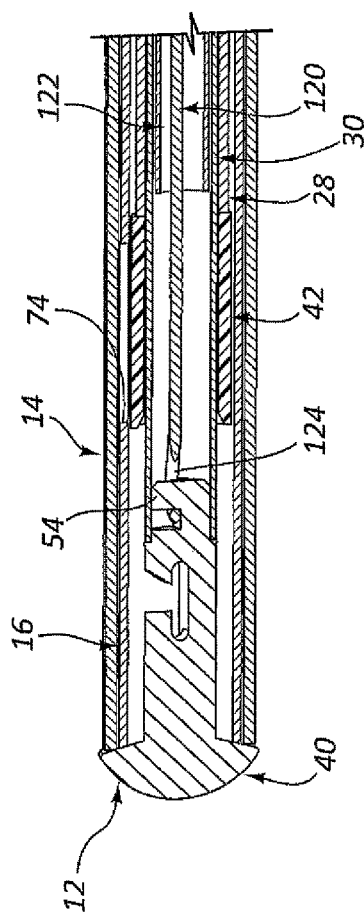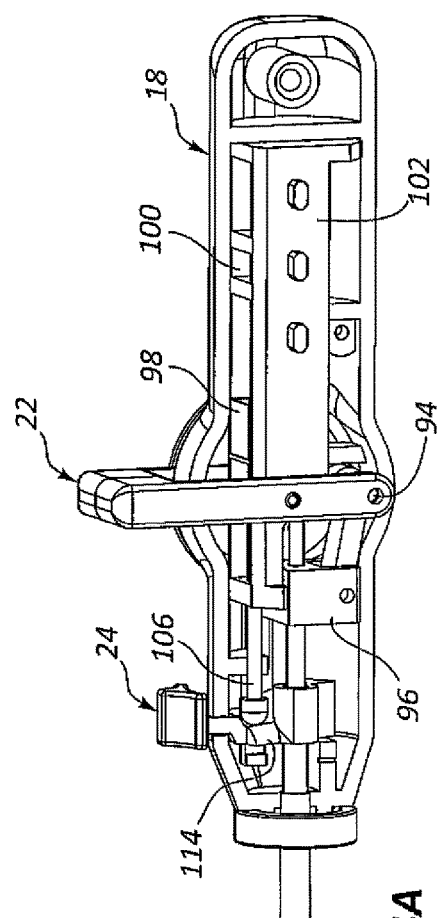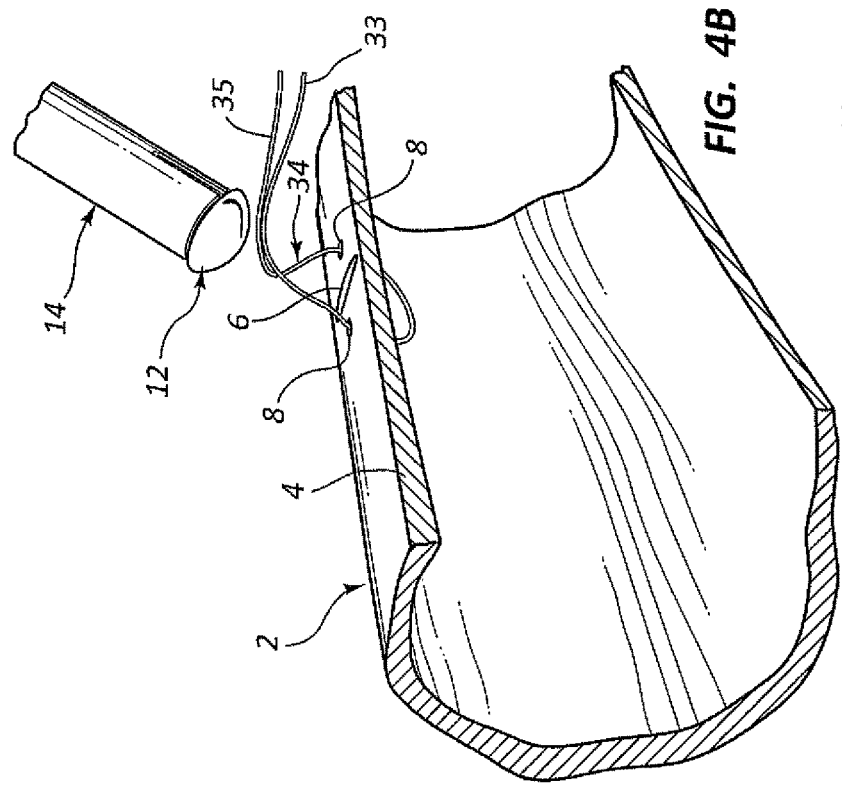
FIG. 4C
FIG. 4B
FIG. 4A

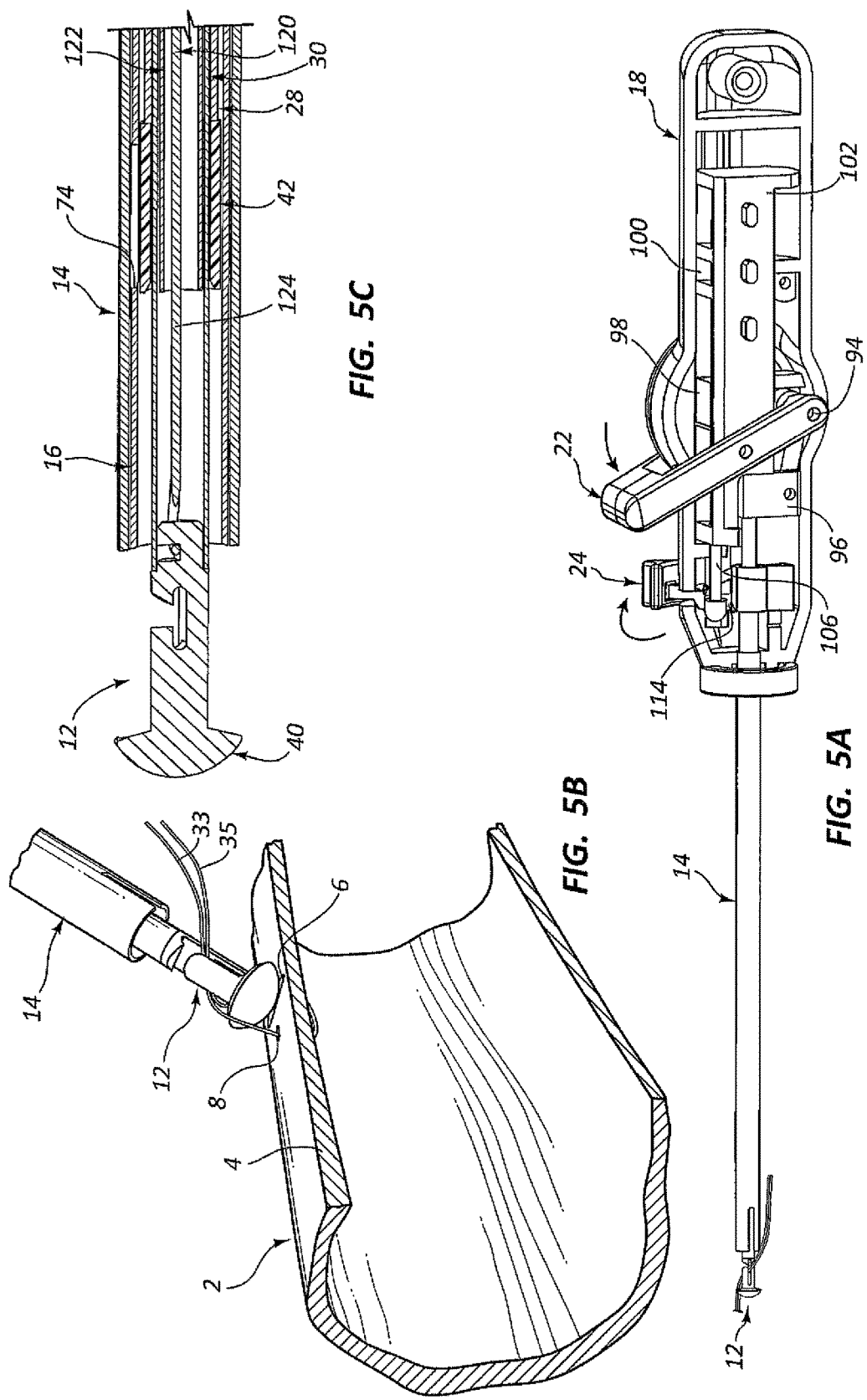

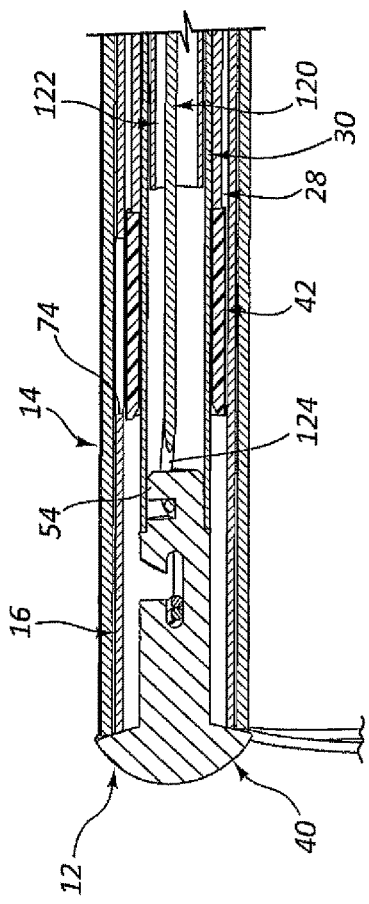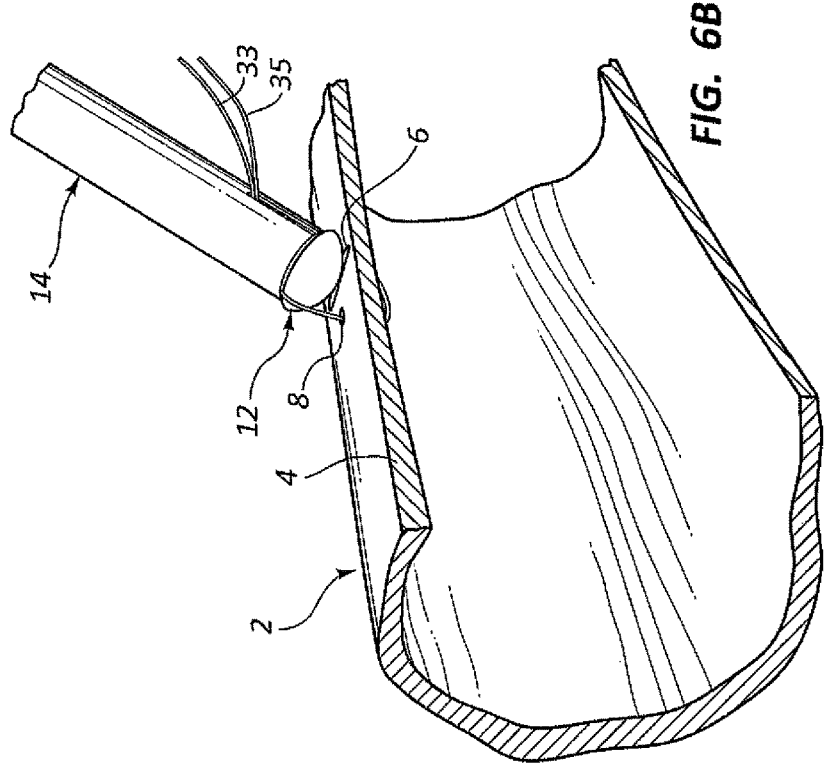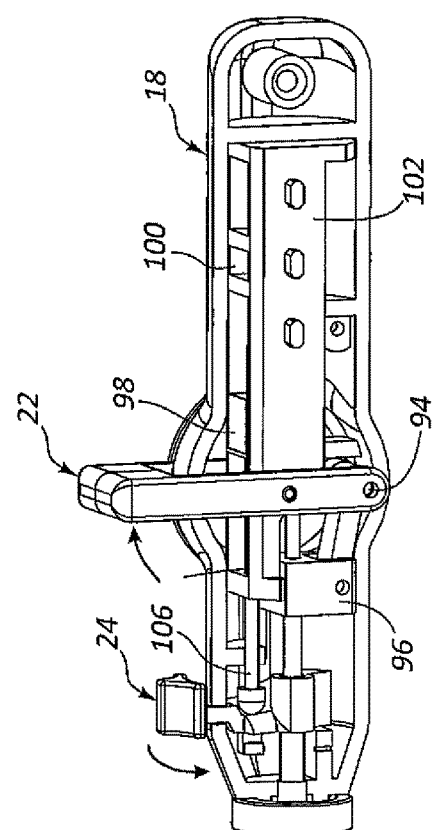

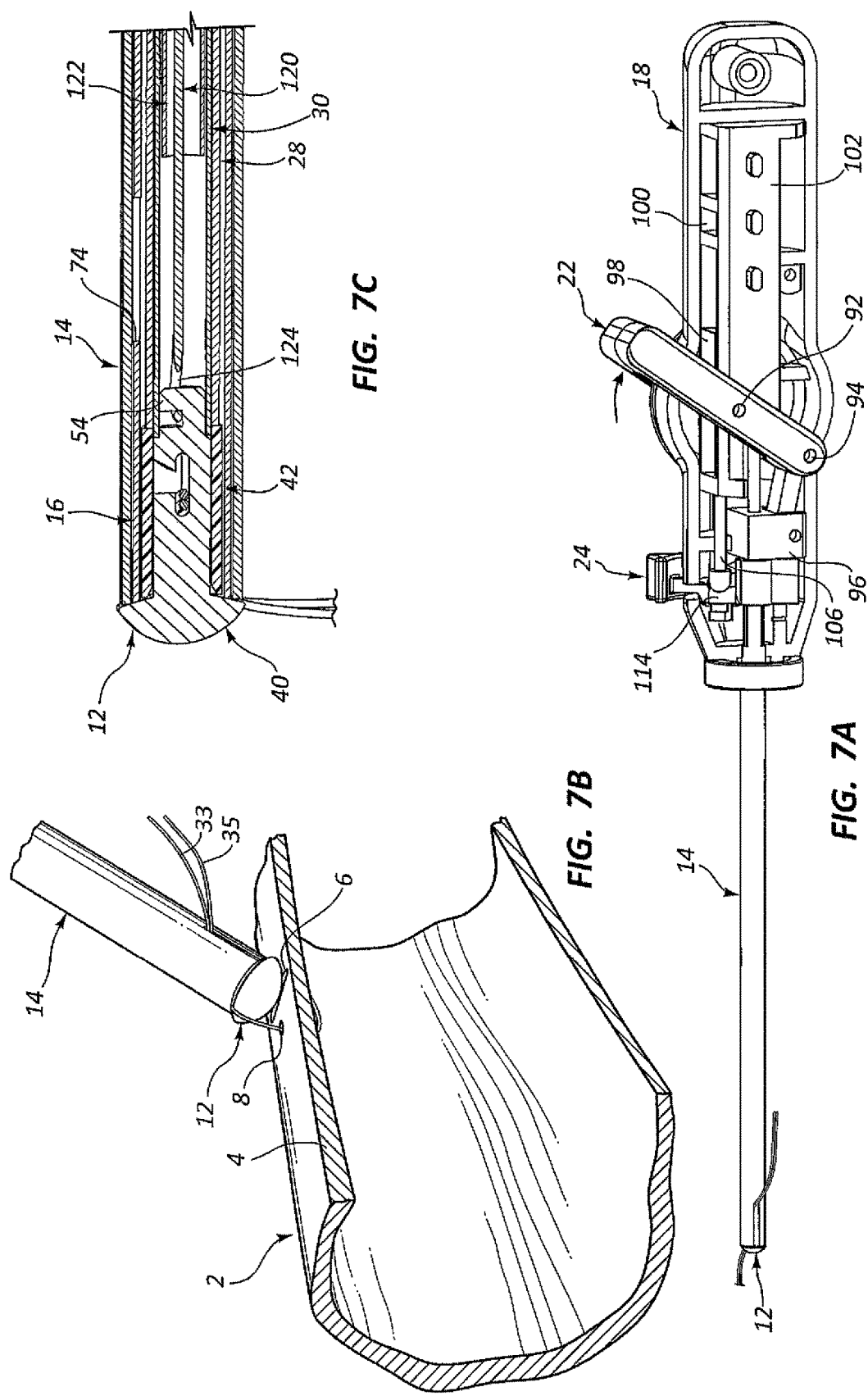

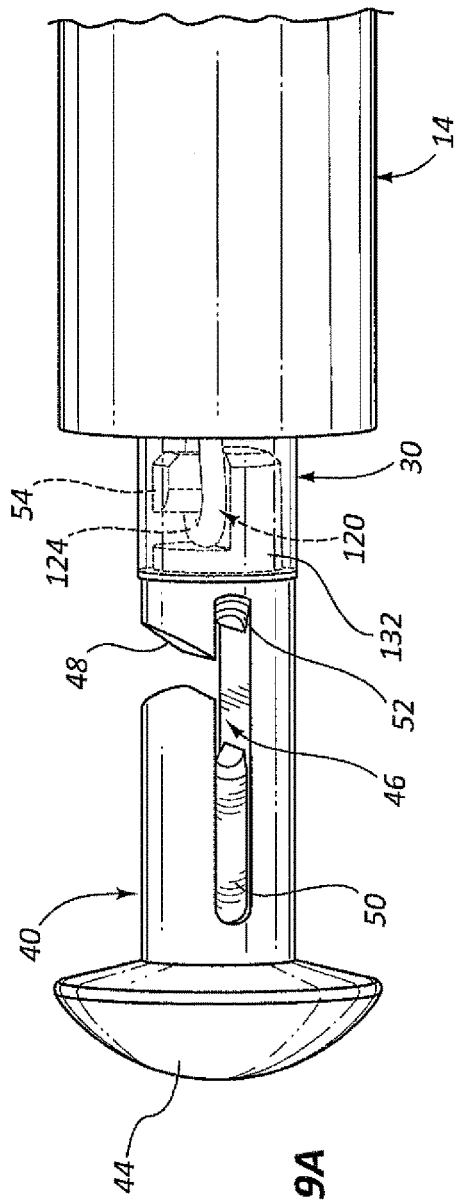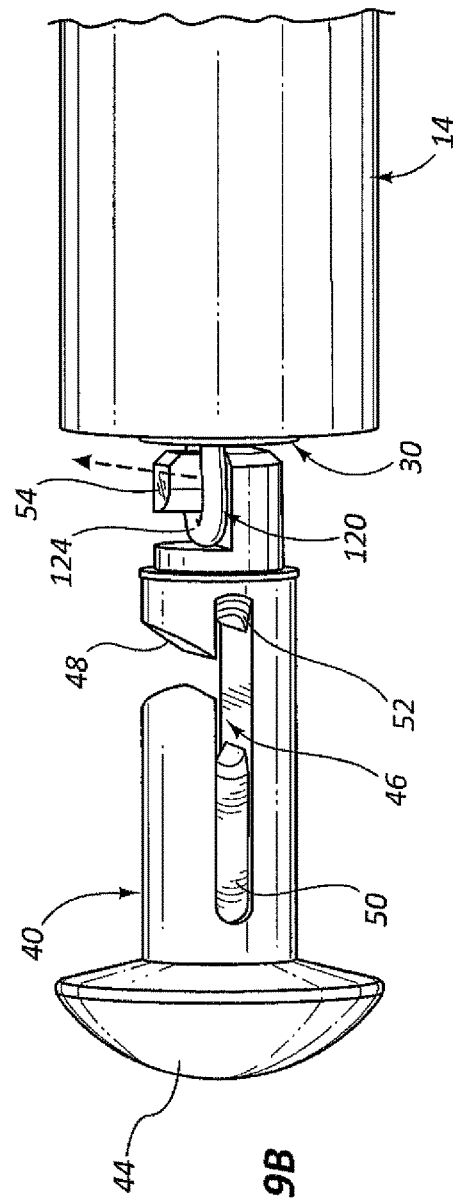
FIG. 9A
FIG. 9B

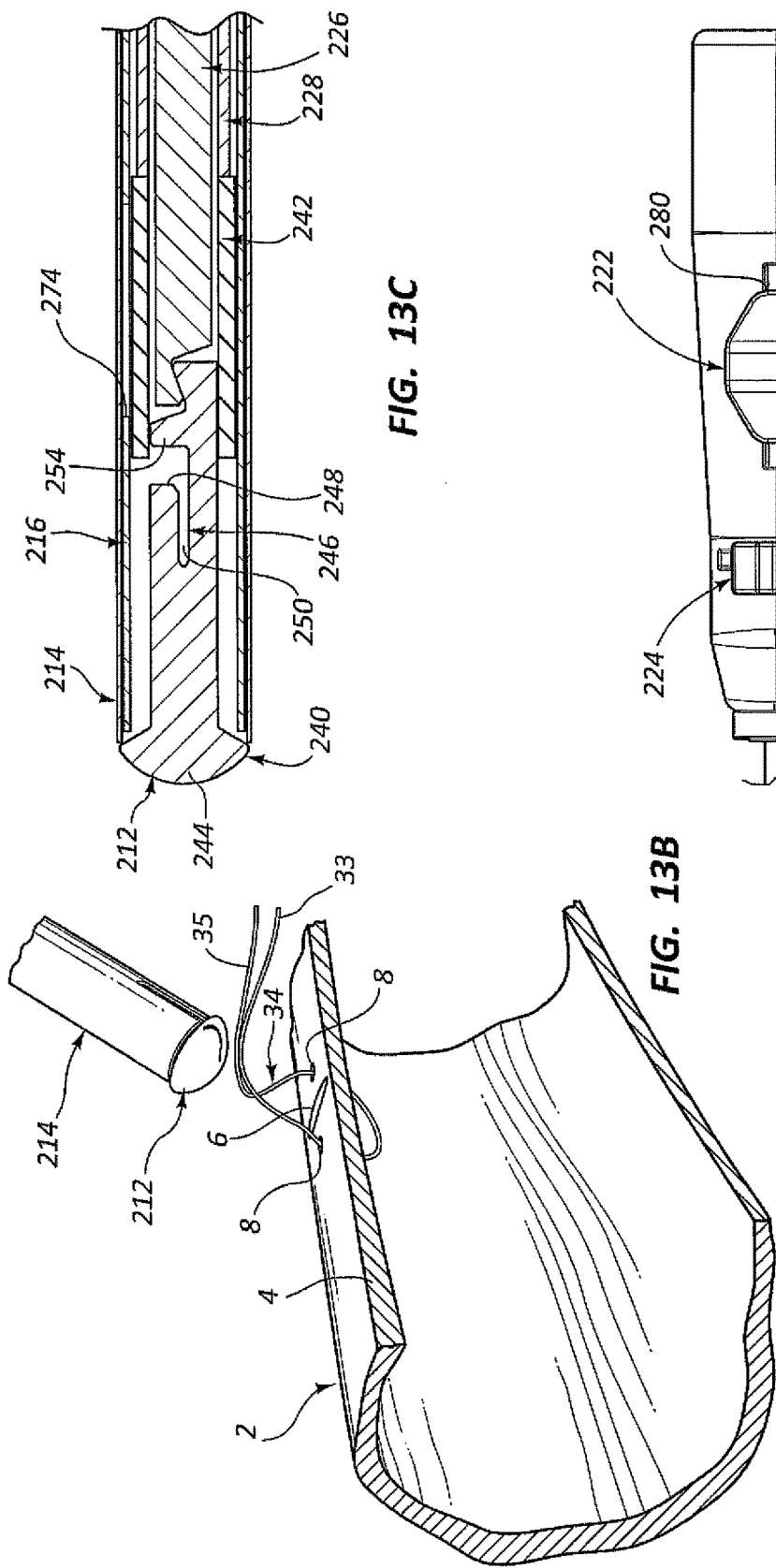

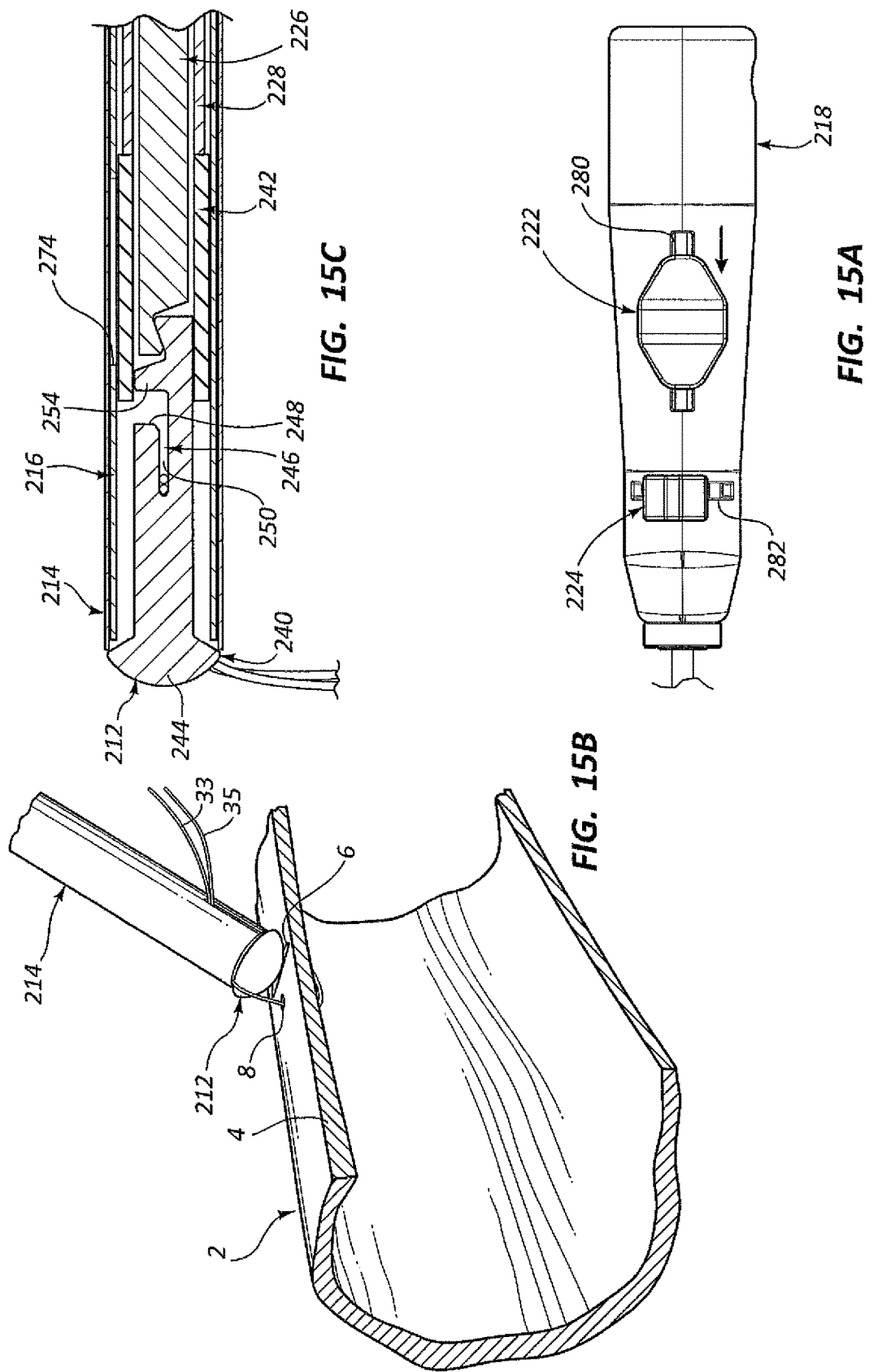

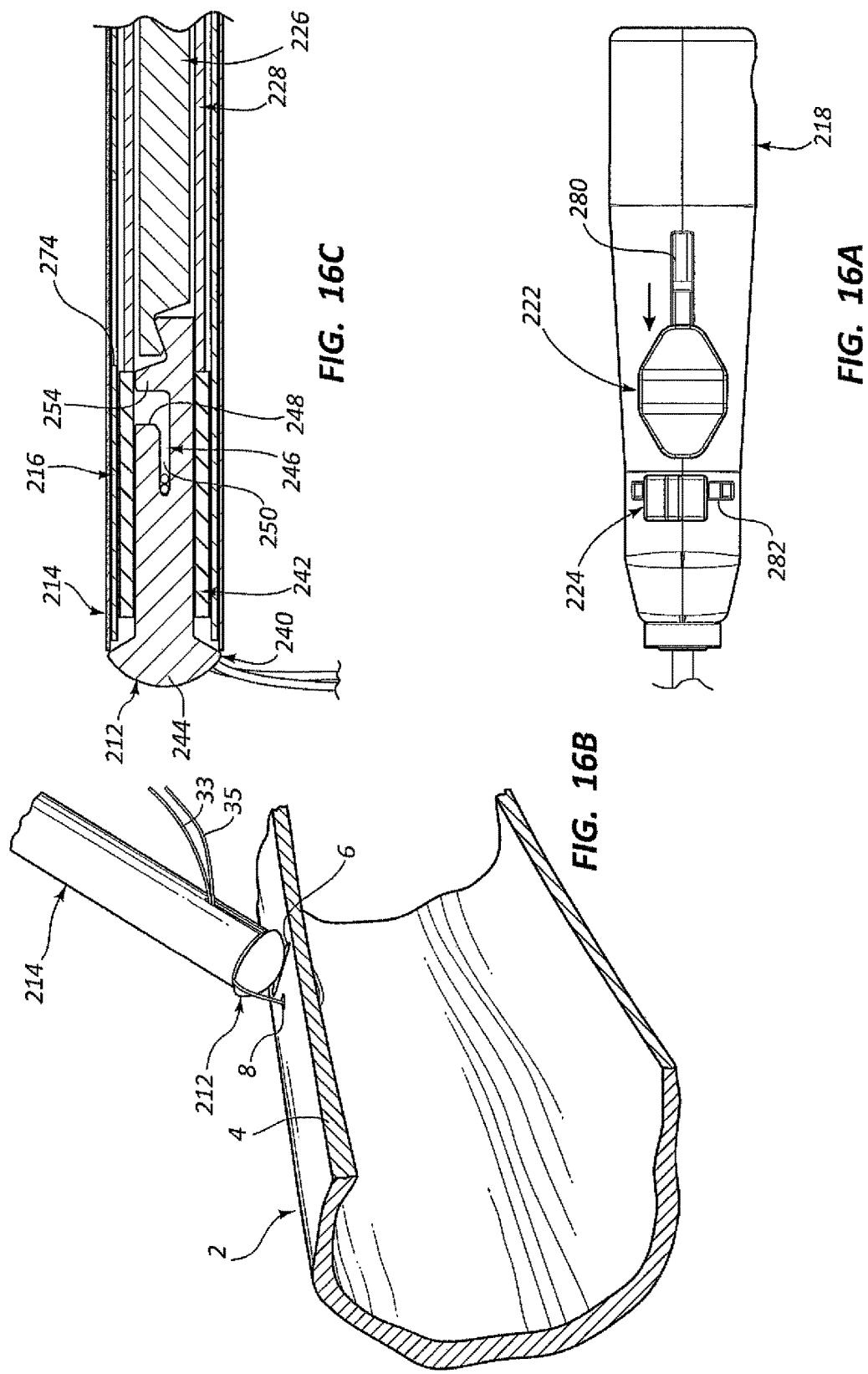

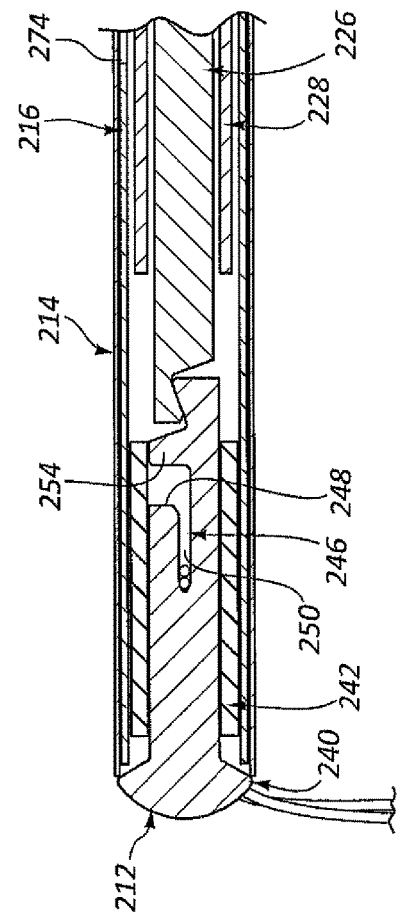
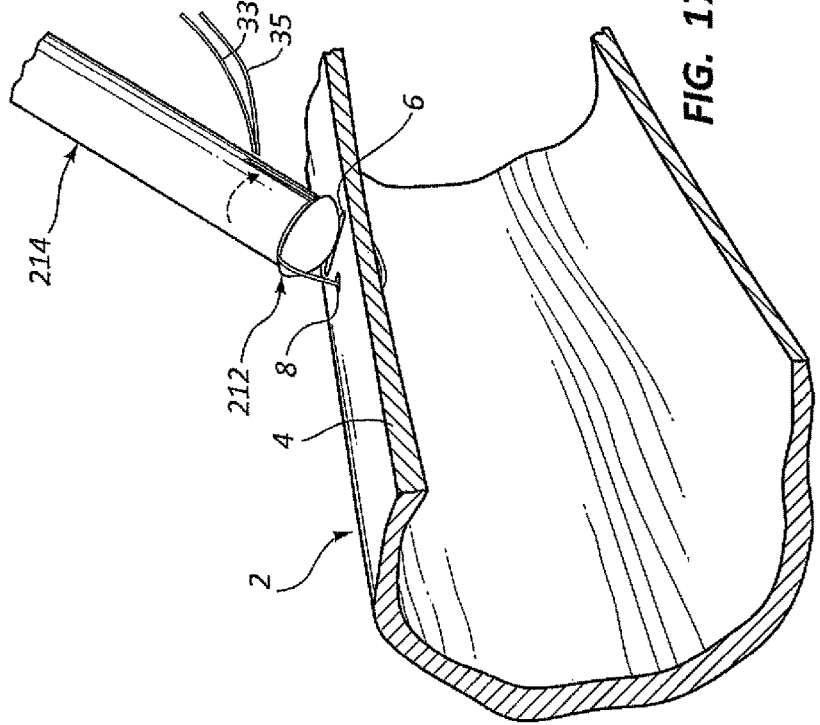
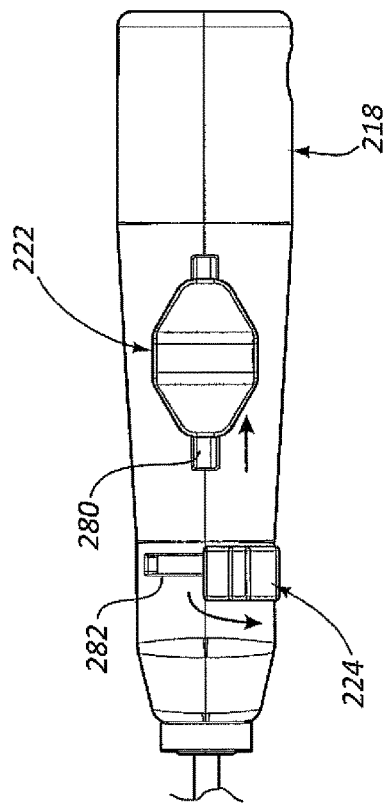
FIG. 17C
FIG. 17A
FIG. 17B

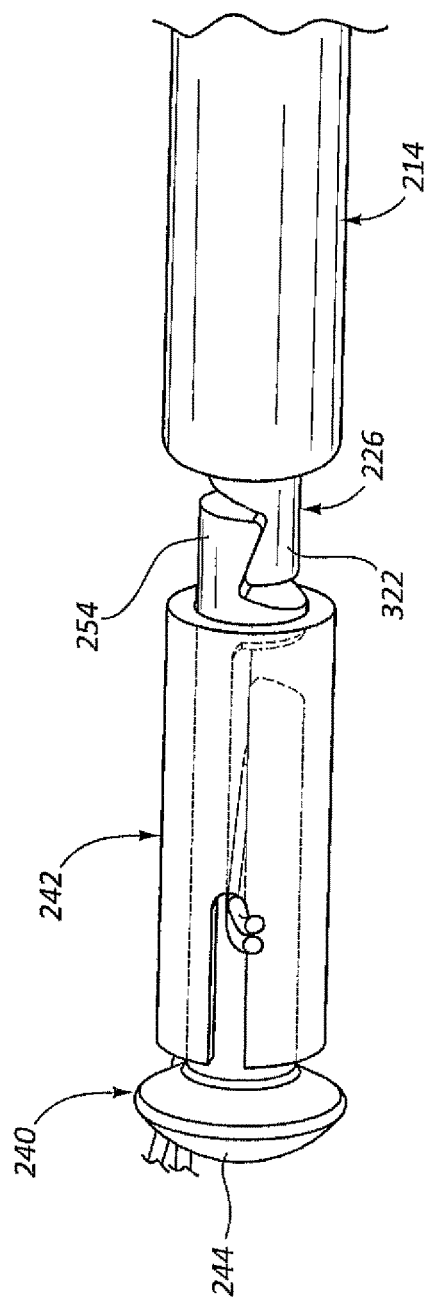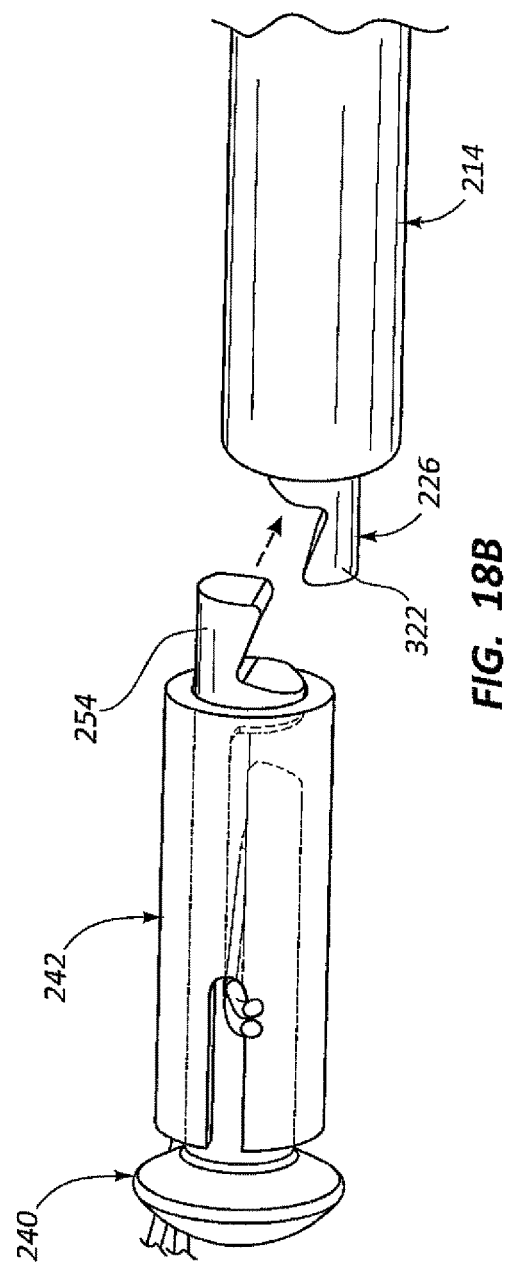
FIG. 18A
FIG. 18B

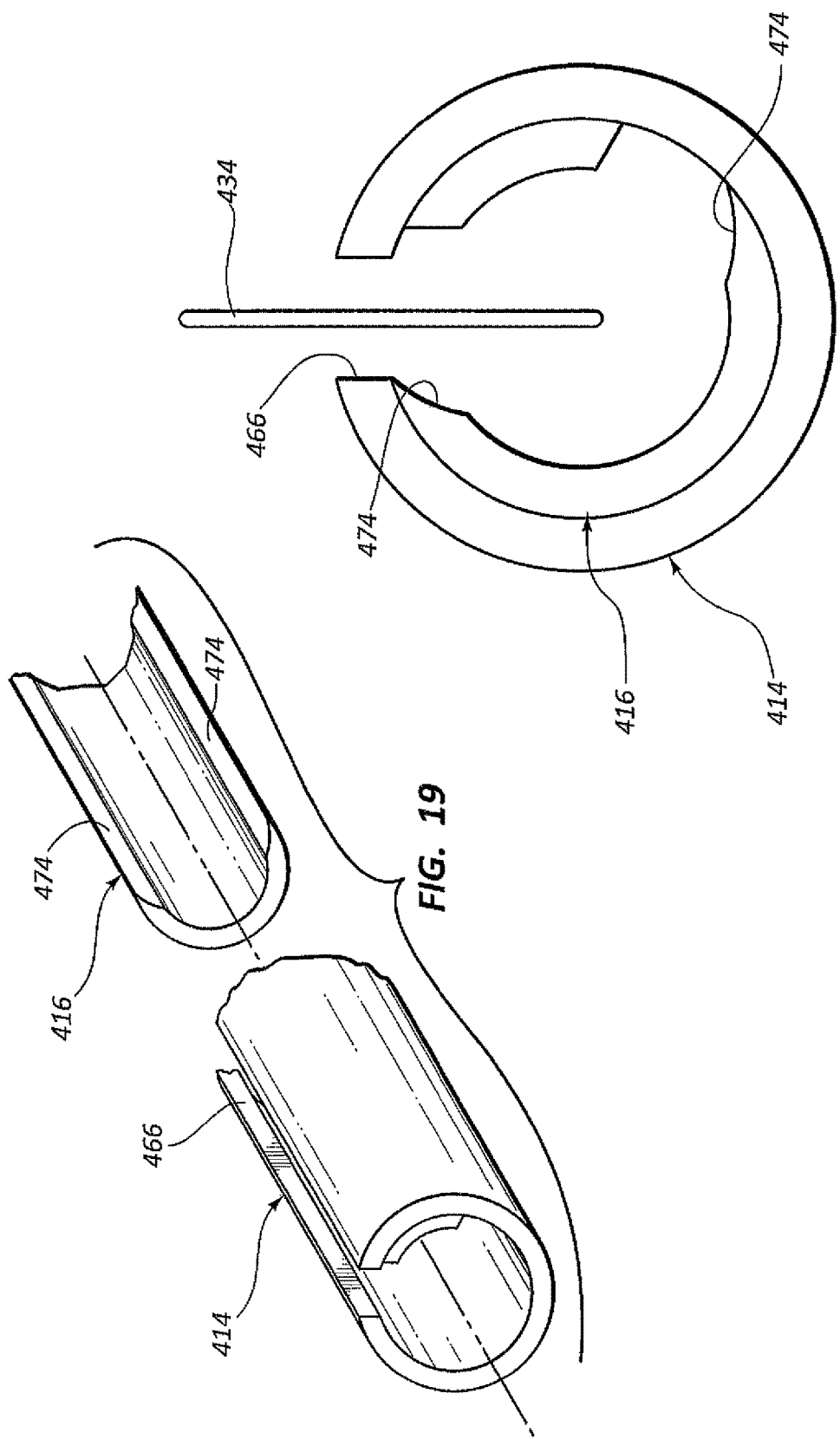

SUTURE LOCKING DEVICE AND METHODS

RELATED APPLICATION

This claims the benefit of U.S. Provisional Application No. 61/474,223, filed 11 Apr. 2011, which is hereby incorporated by reference in its entirety.

TECHNICAL FIELD

The present disclosure relates to closure devices, and more specifically relates to closure devices that hold a vessel opening closed using sutures.

BACKGROUND

Various medical procedures, particularly cardiology procedures, involve accessing a corporeal vessel through a percutaneous sheath. The sheath necessarily requires the formation of a hole or opening in the vessel wall so that a medical procedure may be performed via the sheath. After the particular medical procedure has been performed, the sheath must eventually be removed from the vessel and the access hole in the vessel wall must be closed.

A number of prior vascular closure devices have been developed in attempting to provide a solution for the problem of closing a hole in the vessel wall. Tissue approximation typically involves passing a length of suture into and through adjacent vessel and subcutaneous tissue, across the vessel opening, and back into and through adjacent vessel and subcutaneous tissue. Certain prior closure devices have involved relatively complicated methods and devices for extracting a length of suture from inside the vessel so that the physician can approximate tissue surrounding the hole in the vessel wall through use of the suture.

U.S. Pat. No. 5,643,292 and U.S. Pat. No. 6,059,800 disclose example prior suturing devices used for approximating tissue surrounding the opening in a vessel wall. Most prior closure devices enlarge the vessel opening thereby negating the benefits of using smaller or less invasive percutaneous products. Prior suturing devices are also relatively complicated and difficult to use.

There remains a need, therefore, to provide a suturing apparatus that is relatively simple in construction, is easy to use, and can effectively approximate tissue surrounding an opening in a vessel wall. There is also a need to provide a suturing device that minimizes invasiveness of the suturing procedure.

SUMMARY

One aspect of the present disclosure is directed to a suture locking device that includes a hollow carrier member, a locking assembly, a suture path, a cutter assembly, and an actuator assembly. The hollow carrier member includes a slot formed in a sidewall thereof. The locking assembly is mounted at a distal end of the carrier member and includes first and second locking members. The first locking member has a latch portion, and the second locking member is connectable to the first locking member. The suture path is receptive of a suture and is defined at least in part between the first and second locking members and at least in part within the slot of the carrier member. The actuator assembly is operable to expose the latch portion for receipt of the suture, to draw a portion of a suture into the carrier member along the suture path, to move the first and second locking members together to lock the suture relative to the locking assembly, and to operate the cutter assembly to cut the suture within the carrier member.

The latch portion may have entrance and exit portions across a width of the first locking member, wherein at least one of the entrance and exit portions is radially aligned with the slot in the carrier member. The suture path may exit through the sidewall of the carrier member. The suture locking device may include a handle positioned at a proximal end of the carrier member. The actuator assembly includes a first actuator lever mounted to the handle and operable to move the first and second locking members relative to each other, and a second actuator lever mounted to the handle and configured to operate the cutter assembly. The cutter assembly may include a cutting device positioned in the carrier member and movable across the slot to cut the suture. The cutting device may be operable by rotating relative to the carrier member.

The suture locking device may also include a disconnect member arranged to connect the locking assembly to the handle, wherein operating the second actuator lever disconnects the disconnect member from the locking assembly. The suture locking device may include a locking rod coupled to the actuator assembly and operable to move the first and second locking members relative to each other to lock the suture. The suture locking device may include a sleeve movable with the actuator assembly between a connect position covering a portion of the disconnect member to maintain connect of the disconnect member to the locking assembly, and an disconnect position wherein a portion of the disconnect member is exposed to permit disconnection of the disconnect member from the locking assembly.

Another aspect of the present disclosure relates to a suture locking device that includes a suture locking assembly, a suture cutting member, and an actuator assembly. The actuator assembly includes a first actuator operable longitudinally to lock the suture with the suture locking assembly, and a second actuator operable laterally to cut concurrently the suture with the suture cutting member and disconnect the suture locking assembly from the suture locking device.

The suture locking assembly may include first and second locking members that define a suture path therebetween, wherein moving the first and second locking members relative to each other locks the suture relative to the suture locking assembly. The suture locking device may include a carrier member that is releasably mounted at a distal end of the carrier member. The actuator assembly may include first and second levers, wherein the first lever is coupled to the suture locking assembly and the second lever is coupled to the suture cutting member. The first and second levers may be actuatable in directions perpendicular to each other.

Another aspect of the present disclosure relates to a method of locking a suture across a vessel opening. The method includes providing a suture locking device having a locking assembly, a carrier member, first and second actuators, and a cutting member. The method also includes passing the suture through the locking assembly and through a sidewall of the carrier member, operating the first actuator to lock the locking assembly to the suture, operating the second actuator to cut the suture with the cutting member within the carrier member, and detaching the locking assembly from the suture locking device by operating one of the first or second actuators.

The locking assembly may include first and second locking members, and operating the first actuator to lock the locking assembly to the suture may include capturing the suture between the first and second locking members. Operating the second actuator to cut the suture with the cutting member may include rotating the cutting member relative to the carrier member. Cutting the suture and detaching the locking assembly may include rotating the second actuator about a longitudinal axis of the suture locking device.

The suture locking device may further include a handle mounted at a proximal end of the carrier member and the first actuator may include a lever mounted to the handle. Operating the first actuator to lock the locking assembly may include moving the lever longitudinally relative to the handle, and operating the second actuator to cut the suture may include rotating the lever laterally relative to the handle. The suture locking device may include a disconnect member coupled to the locking assembly at a distal end and coupled to one of the first and second actuators at a proximal end. Disconnecting the locking assembly from the suture locking device may include uncovering a portion of the locking assembly to permit disconnection of the disconnect member from the locking assembly.

A further aspect of the present disclosure relates to a method of operating a suture locking device. The method includes providing the suture locking device with a locking assembly, a carrier member, an actuator assembly, and a cutting member, wherein the locking assembly includes first and second locking members mounted to the carrier member. The method also includes operating the actuator assembly to connect the first and second locking members in a locked position, operating the actuator assembly to move the cutting member relative to the carrier member, and disconnecting the locking assembly from the carrier member concurrently with operating the actuator assembly to connect the first and second locking members, or operating the actuator assembly to move the cutting member relative to the carrier member.

The suture locking device may include a handle, and the actuator assembly may include first and second levers mounted to the handle. Operating the actuator assembly to move the first and second locking members into a locked position may include moving the first lever longitudinally relative to the handle, and operating the actuator assembly to move the cutting member may include rotating the second lever relative to the handle. The method may also include passing a suture laterally through the locking assembly prior to operating the actuator assembly to connect the first and second locking members in a locked position.

The foregoing and other features, utilities, and advantages of the invention will be apparent from the following detailed description of the invention with reference to the accompanying drawings.

BRIEF DESCRIPTION OF THE DRAWINGS

FIG. 4A illustrates an actuator assembly of the suture locking device of FIG. 1 in a rest state prior to connecting to a suture.

FIG. 4B is a detailed end view of the suture locking device of FIG. 4A.

FIG. 4C is a cross-sectional view of a distal end of the suture locking device of FIG. 4A.

FIGS. 5A-C illustrate the suture locking device of FIG. 1 in a loading position.

FIGS. 6A-C illustrate the suture locking device of FIG. 1 in a suture capture position.

FIGS. 7A-C illustrate the suture locking device of FIG. 1 in a suture lock position.

FIG. 9A illustrates a distal end of the suture locking device of FIG. 1 with the locking assembly in an attached position.

FIG. 9B illustrates the locking assembly of FIG. 9A in a detached position.

FIGS. 13A-C illustrate the suture locking device of FIG. 10 in a rest state prior to attaching to a suture.

FIGS. 15A-C illustrate the suture locking device of FIG. 10 in a loaded state with a suture captured therein.

FIGS. 16A-C illustrate the suture locking device of FIG. 10 in a suture locked state.

FIGS. 17A-C illustrate the suture locking device of FIG. 10 in a suture cutting state.

FIG. 18A illustrates a distal end of the suture locking device of FIG. 10 with the locking assembly in an attached position.

FIG. 18B illustrates the locking assembly of FIG. 18A in a detached position.

FIG. 19 is an exploded perspective view of another example cutting arrangement according to the present disclosure.

FIG. 20 is an end view of the cutting arrangement of FIG. 19 assembled together.

DETAILED DESCRIPTION

Figure 1:
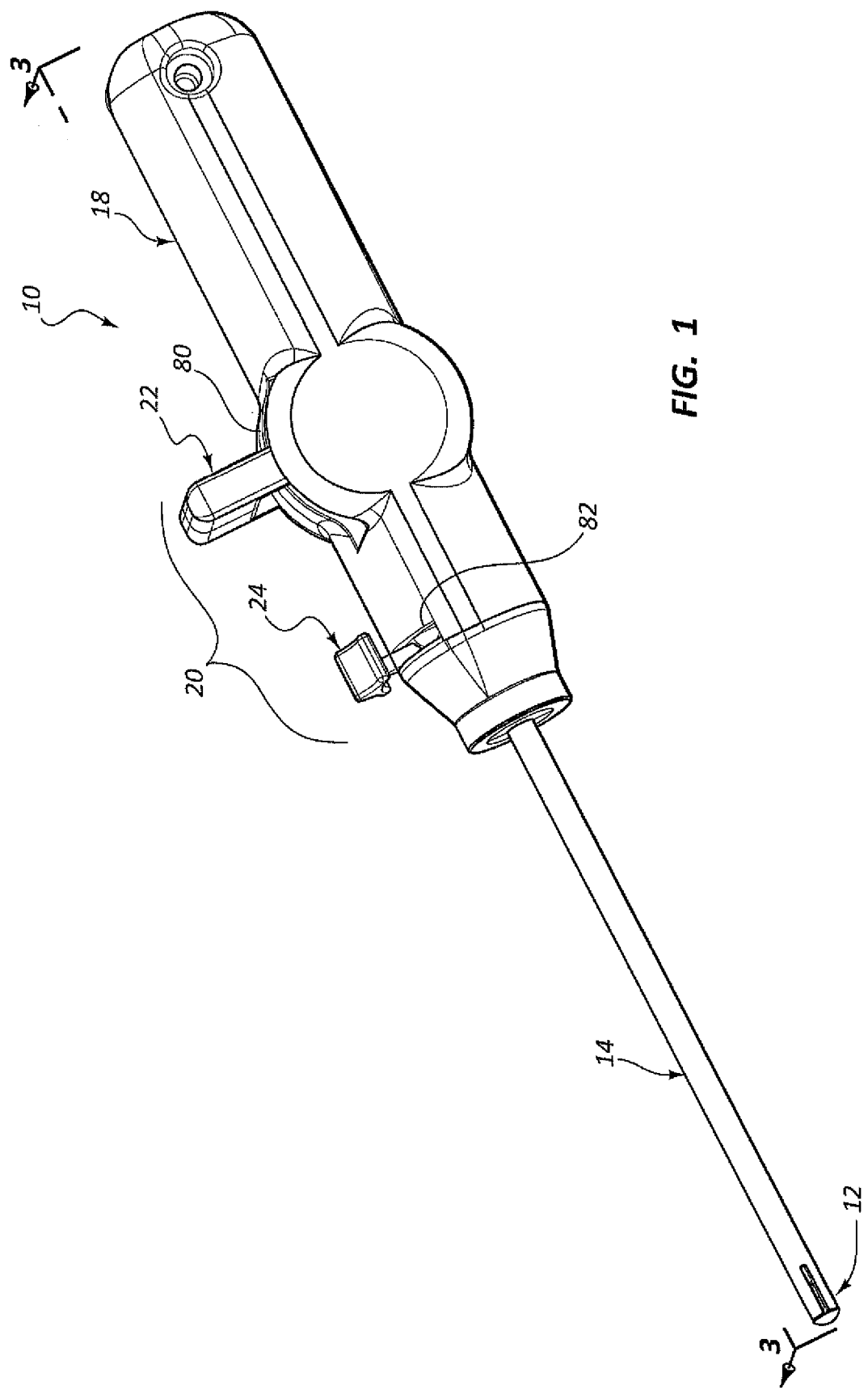
FIG. 1 is a perspective view of an example suture locking device in accordance with the present disclosure.

The suture locking devices of the present disclosure may be particularly useful for closing a tissue puncture that is positioned percutaneously below an outer tissue surface. In one application, the tissue puncture is a vessel puncture positioned within a tissue layer spaced from an outer tissue surface. The vessel puncture is accessible percutaneously through a tissue tract. The tissue puncture is closed using a knot that is tied in the suture and then advanced down the tissue tract to the tissue puncture. The tissue puncture is often hidden from an operator's view, making it difficult to confirm visually whether the knot is properly positioned and the tissue puncture sealed closed.

The present disclosure is directed to a device that locks at least one suture in place across a wound (e.g., to cinch closed a puncture in a vessel). The device may be constructed to help close a tissue puncture that is hidden within a tissue tract and accessible percutaneously. In one embodiment, the device is adapted to lock a pair of suture strands (e.g., opposing ends of a single suture) across an opening in a wall of a vessel. The present disclosure contemplates that a medical procedure will be performed through a sheath inserted through the opening in the vessel wall to access the inside of the vessel. The device is used after the medical procedure has been completed and the sheath removed. A closure device may be used to place the suture extending through the vessel wall adjacent to the vessel opening. The device of the present disclosure may be used to advance a locking device along the suture to the vessel opening. The locking device cinches the suture to close the vessel opening and then hold the suture in tension to maintain closure of the vessel opening.

In one example, the suture locking device includes a locking assembly with a multi-piece construction. The suture is captured between at least two of the locking assembly pieces. When the locking assembly is in an unlocked state or position, the suture is able to move freely through the locking device. When the locking assembly is moved into a locked state or position, the suture is locked (e.g., immovable at least longitudinally) in place relative to the locking assembly.

The suture locking device may include a suture cutting feature that cuts the suture after locking the suture in place relative to the locking assembly. The suture locking device may include an actuator assembly that includes first and second actuators. The first actuator moves between first and second positions to operate the locking assembly to lock the suture in place. The second actuator may move between first and second positions to operate a cutting device to cut the suture. Locking the locking device may include actuation of the first actuator along a length of the device (e.g., translational movement in a longitudinal direction, or rotational or pivotal movement about a lateral axis of the device). Cutting the suture may include actuation of the second actuator laterally (e.g., rotation or pivoting about a longitudinal axis of the device).

Referring now to FIGS. 1-9B, an example suture locking device 10 is shown and described. The suture locking device 10 includes a locking assembly 12, a carrier member 14, a cutting device 16, a handle 18, an actuator assembly 20, a disconnect member 26, a locking rod 28, and a sleeve 30. A suture path is defined through the suture locking device 10 as shown in, for example, FIGS. 6A-C. The suture locking device 10 is operable to load a suture 34, lock the suture relative to the locking assembly 12, and cut the suture 34 with the cutting device 16. See FIGS. 4A-8C. The suture 34 may be positioned extending across a puncture 6 in a vessel wall 4 of a vessel 2 (see FIG. 4B). The suture 34 may extend through one or more suture openings 86 positioned adjacent to the puncture 6. In some arrangements, the suture 34 extends across the puncture 6 on an internal side of the vessel wall 4, and the locking assembly 12 is used to maintain pressure or tension in the suture 34 to hold the puncture 6 closed on an outer surface of the vessel wall 4 using the locking assembly 12.

Figure 2A:
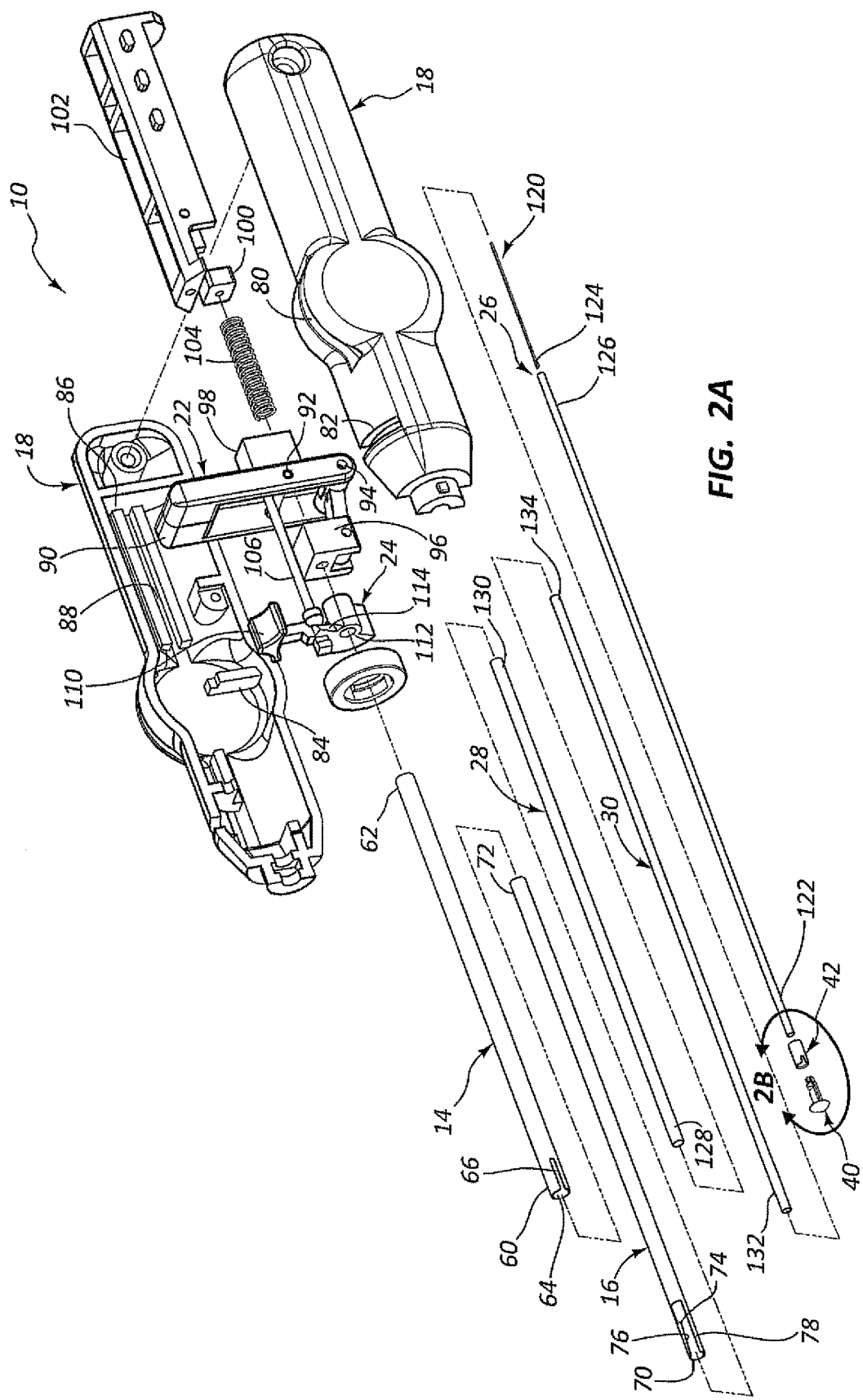
FIG. 2A is an exploded perspective view of the suture locking device of FIG. 1.
Figure 2B:
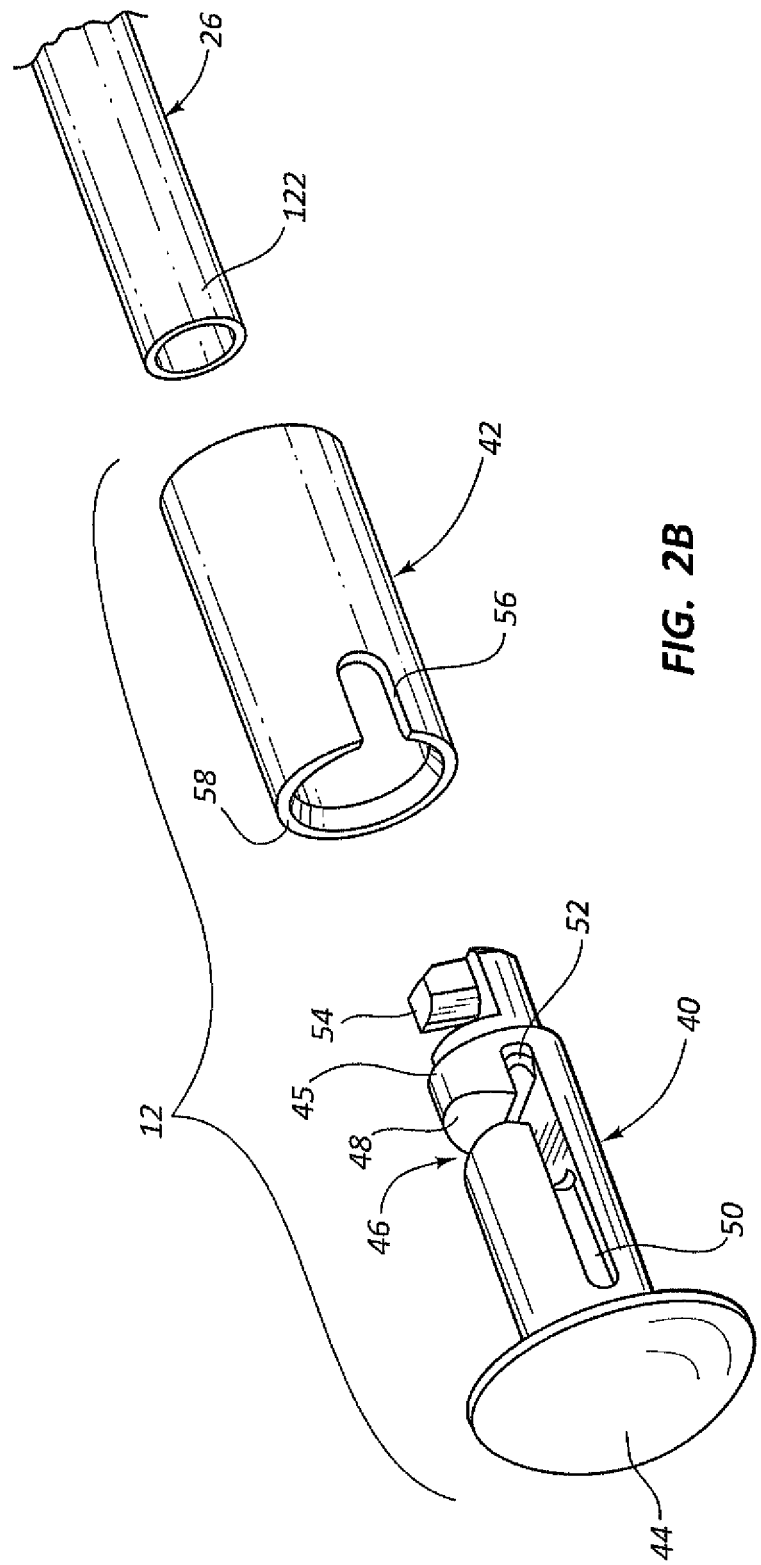
FIG. 2B is a detailed view of a locking assembly of the suture locking device of FIG. 2A.

Referring to FIG. 2B, the locking assembly 12 includes first and second locking members 40, 42, which are axially movable relative to each other. The first locking member 40 includes a distal surface 44, a latch recess 46, and a retention protrusion 54. The latch recess 46 includes an opening 48, and distal and proximal portions 50, 52. The suture 34 may be positioned within the latch recess 46 and extend laterally through the first locking member 40. The suture 34 may reside in either the distal or proximal portion 50, 52 when loading the suture into the locking assembly 12 and prior to moving the locking assembly 12 into a loaded position or the locked position as will be described in further detail below.

The second locking member 42 includes a locking recess or slot 56, which is open at a distal end 58 of the second locking member 42. The locking recess 56 may be aligned radially and circumferentially with the latch recess 46 so that the suture 34 positioned in the latch recess 46 may also extend through the locking recess 56.

In some arrangements, the latch recess 46 may include only one or the other of the distal and proximal portions 50, 52. The distal and proximal portions 50, 52 may be defined as undercut features or latch features that help retain the suture 34 within the latch recess 46. In some arrangements, the opening 48 may define the entire latch recess 46 without distal and proximal portions 50, 52. In some arrangements, the second locking member 42 may include a plurality of locking recesses 56 spaced around the periphery of the second locking member 42. In other arrangements, the second locking member 42 is void of recesses, apertures, or other features that help retain the suture 34.

In operation, the first and second locking members 40, 42 move longitudinally relative to each other to capture the suture 34 therebetween. In one arrangement, the proximal end 58 of the second locking member 42 is moved longitudinally (e.g., advanced distally) toward the latch recess 46 to capture the suture 34 between the proximal end 58 and the distal portion 50 of the latch recess 46. The locking assembly 12 may apply pressure on the suture 34 to compress at least partially the suture 34, and maintain that applied pressure. The suture 34 captured in this way may provide a locked state or locked position for the locking assembly 12. In other arrangements, the suture 34 may be captured between an internal surface of the second locking member 42 and an external surface of the first locking member 40 in which the suture 34 is compressed or pinched to provide the locked state or locked position for the locking assembly 12.

In some arrangements, the first and second locking members 40, 42 may include features that provide a connection between the first and second locking members to provide the locked state or locked position. In one example, the first and second locking members 40, 42 may move into an interference fit, snap fit, or latched orientation when moved toward each other to provide the locked state or locked position for the locking assembly 12.

The retention protrusion 54 of the first locking member 40 may be constructed to effect a releasable connection with the disconnect member 26. Moving the disconnect member 26 out of contact with the retention protrusion 54 may permit release of the locking assembly 12 from the suture locking device 10.

The carrier member 14 may include distal and proximal ends 60, 62, a distal opening 64, and at least one suture opening 66 (see FIG. 2A). The locking assembly 12 may be mounted or positioned at the distal end 60. The carrier member 14 may be mounted or connected to the handle 18 at the proximal end 62. In some arrangements, the carrier member 14 may be fixed to the handle 18. In other arrangements, the carrier member 14 may be movable (e.g., axially movable) relative to the handle 18.

Typically, the cutting device 16, disconnect member 26, locking rod 28 and sleeve 30 are all positioned within and carried by the carrier member 14 in a coaxial arrangement. In some embodiments, each of the cutting device 16, disconnect member 26, locking rod 28 and sleeve 30 may be movable relative to the carrier member 14 (e.g., axially or rotationally movable).

The cutting device 16 includes distal and proximal ends 70, 72, a tab 74 defining a cutting surface 76, and a suture slot 78 (see FIG. 2A). The tab 74 is positioned at the distal end 70 and may define in part the distal end 70 of the cutting device 16. The proximal end 72 of the cutting device 16 is coupled to the actuator assembly 20 as will be described in further detail below. The suture slot 78 may be aligned with the suture opening 66 of the carrier member 14. The suture slot 78 and suture opening 66 may be arranged to receive the suture 34 when the suture 34 is loaded within the suture locking device 10 (see FIGS. 6A-C), during locking of the locking assembly 12 (see FIGS. 7A-C), and during cutting of the suture (see FIGS. 8A-C).

When the suture 34 is positioned within the suture opening 66 and suture slot 78, relative rotation between the carrier member 14 and cutting device 16 captures or pinches the suture 34 between the cutting surface 76 and an edge of the suture opening 66 to cut the suture 34. The suture 34 may be cut within the carrier member 14.

The handle 18 includes a first actuator slot 80, a second actuator slot 82, a first stop member 84, a second stop member 86, and a track 88. The first actuator slot 80 is receptive of a first actuator 22 of the actuator assembly 20. The first actuator slot 80 is oriented longitudinally along a length of the handle 18. The first actuator slot 80 may include at least one opening or slot in some arrangements, and in other arrangements may include a plurality (e.g., a pair) of slots receptive of different portions of the first actuator 22.

The second actuator slot 82 is defined laterally across a width or around a circumference of the handle 18. The second actuator slot 82 is configured to receive a portion of a second actuator 24 of the actuator assembly 20, The second actuator slot 82 may define a single opening or slot in the handle 18, or in other arrangements may define a plurality (e.g., a pair) of slots that receive different portions of the second actuator 24.

The first and second stop members 84, 86 may define stop positions or surfaces internal of the handle 18 for operation of various features of the actuator assembly 20. The first and second stop members 84, 86 may define, for example, a support surface for a biasing member, a stop position for a moving part of the actuator assembly 20, or a pivot or rotation surface. The track 88 may define a pathway for longitudinal movement of a portion of the actuator assembly 20 within the handle 18.

The first actuator 22 of the actuator assembly 20 includes a first lever 90, first and second pivot points 92, 94, first, second, and third connectors 96, 98, 100, a slider 102, a biasing member 104, and a follower 106. The first lever 90 extends through the handle 18 within the first actuator slot 80. The first lever 90 may be operable in a generally longitudinal direction. The first lever 90 may pivot about one of the first and second pivot points 92, 94 during operation of the actuator assembly 20.

The first connector 96 may be referred to as a first block or first base. The locking rod 28 may be connected to the first connector 96 so that movement of the first connector 96 provides movement of the locking rod 28. The second connector 98 may be referenced as a second block or second base. The second connector 98 may be connected to the sleeve 30 so that movement of the second connector 98 provides movement of the sleeve 30. The third connector 100 may be referenced as a third block or third base. The third connector 100 may be connected to disconnect member 26 so that movement of the third connector 100 provides movement of the disconnect member 26. In some arrangements, the follower 106 may also be connected to the second connector 98 so that movement of the follower 106 or movement of the sleeve 30 provides corresponding movement of the other of the follower 106 and the sleeve 30.

Figure 3:
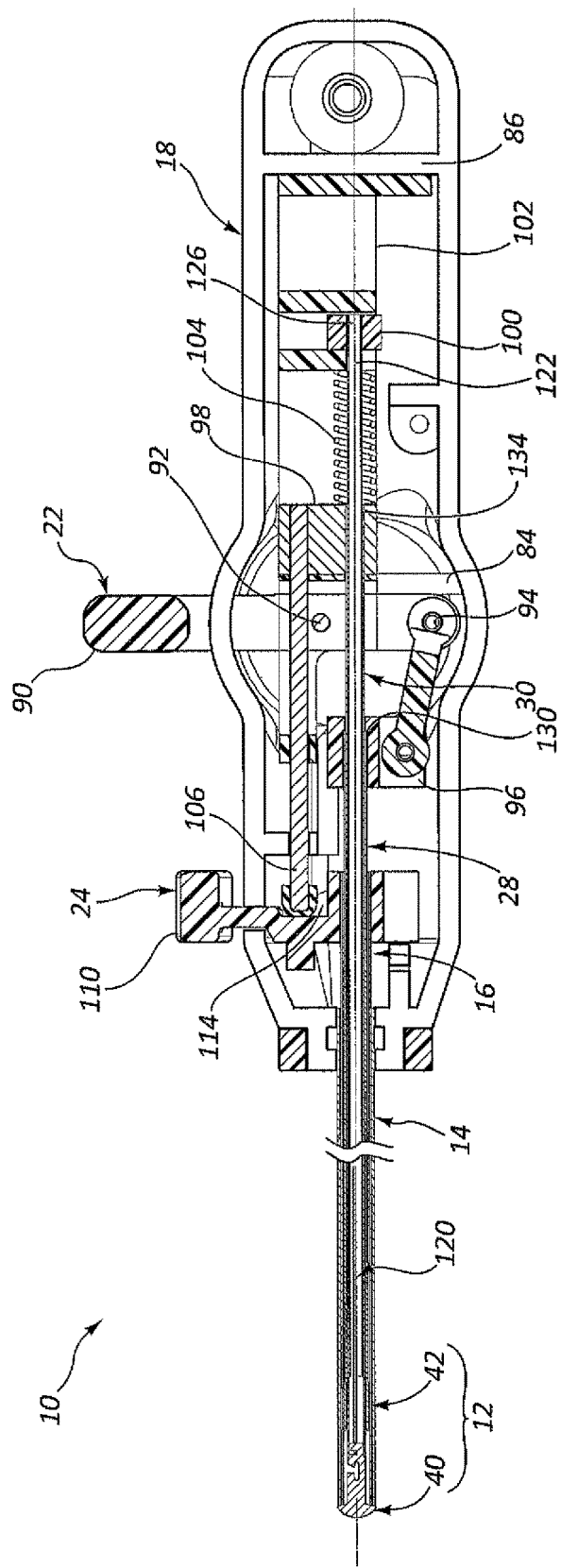
FIG. 3 is a cross-sectional view of the suture locking device of FIG. 1 taken along cross-section indicators 3-3.
Figure 8C:
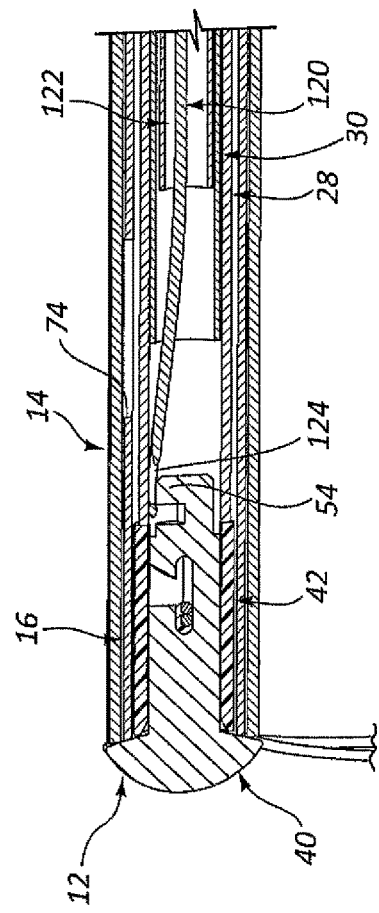
FIGS. 8A-C illustrate the suture locking device of FIG. 1 in a suture cutting position.
Figure 8B:
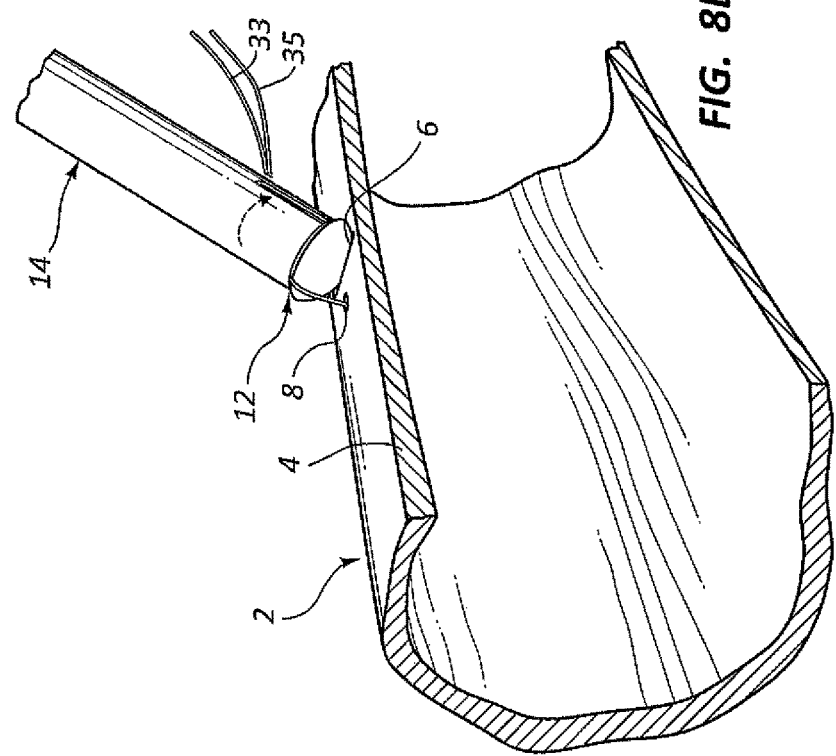
Figure 8A:
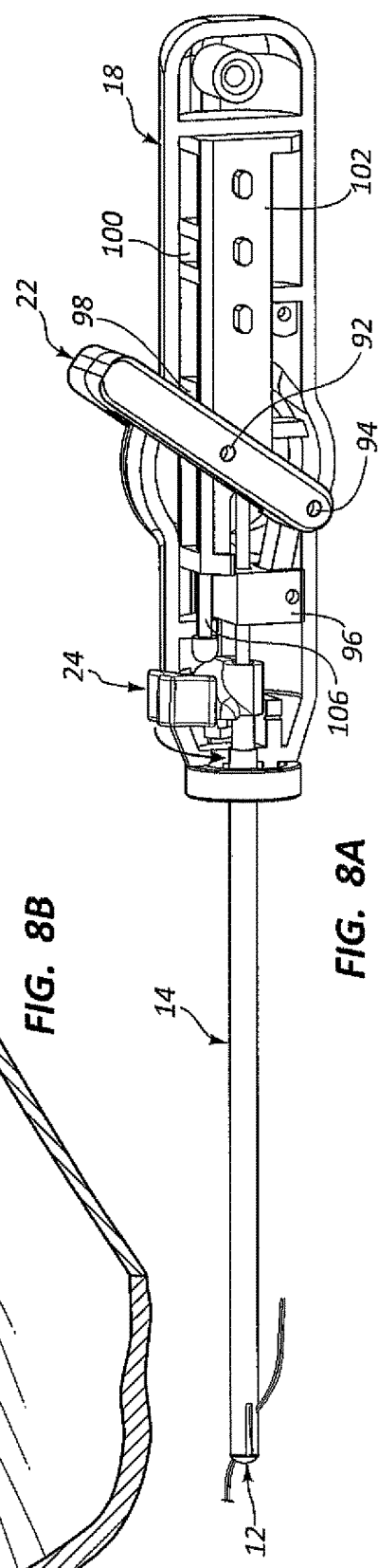
Figure 8D:
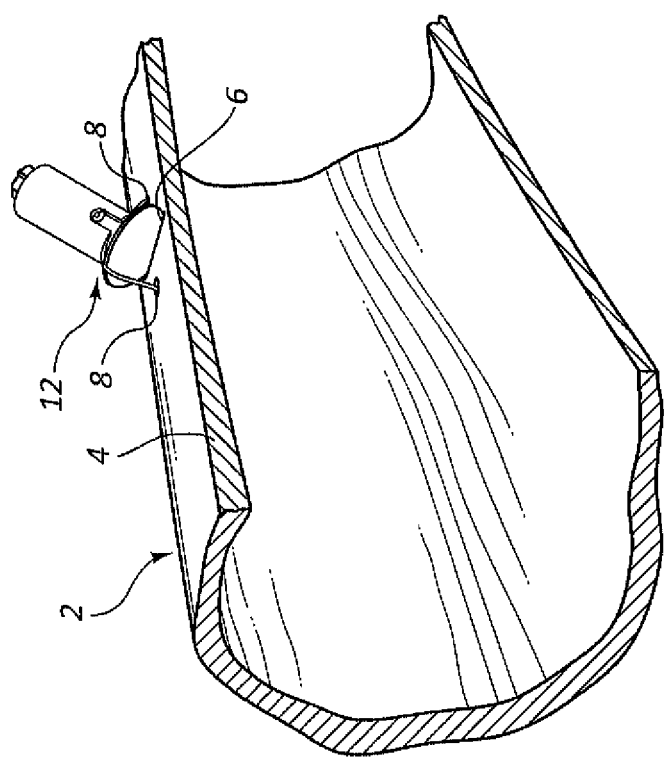
FIG. 8D illustrates the suture locking device of FIG. 1 in a deployed position.
Figure 10:
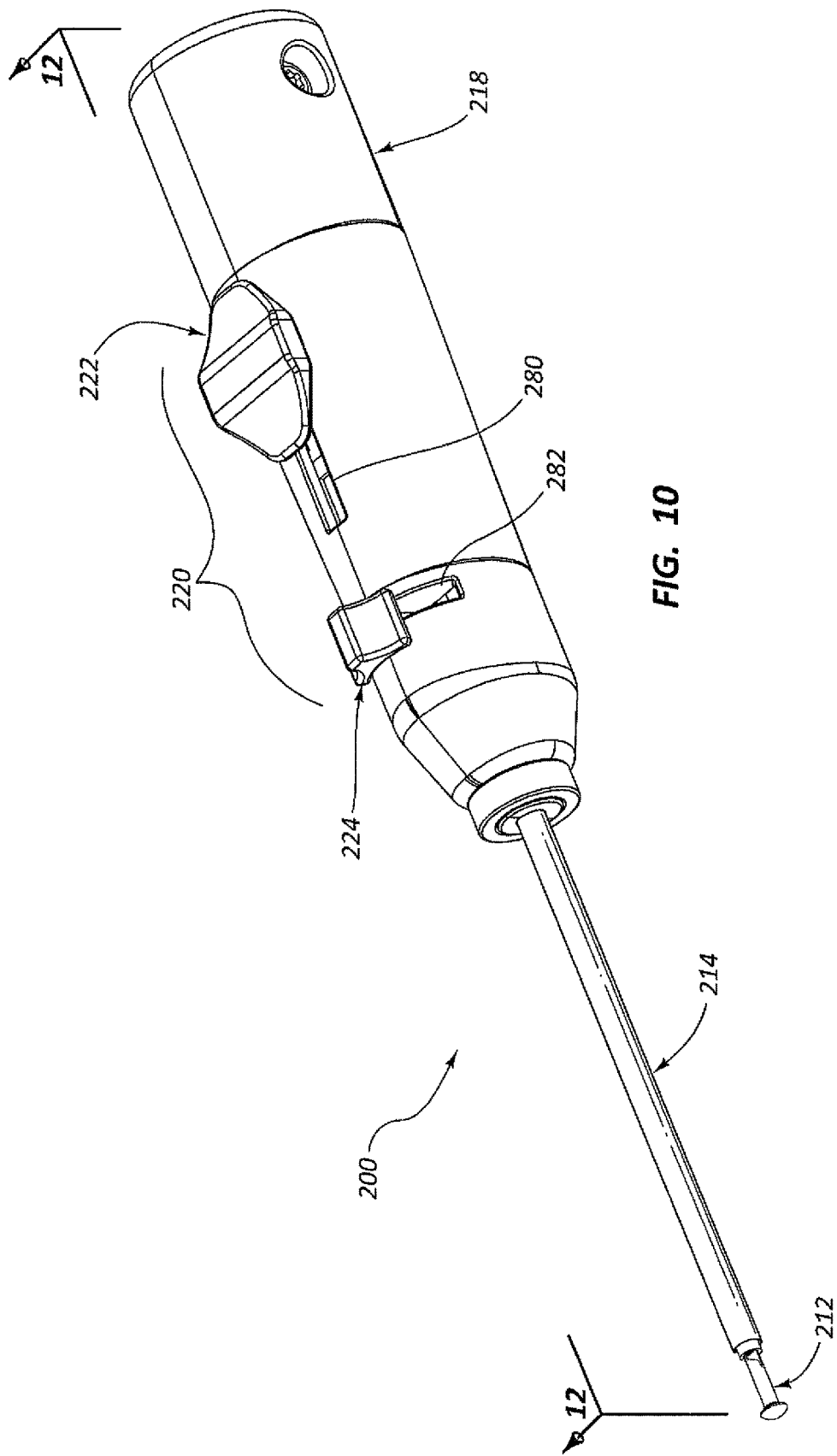
FIG. 10 is a perspective view of another example suture locking device in accordance with the present disclosure.

The second and third connectors 98, 100 may be coupled to the slider 102. In some arrangements, the second and third connectors 98, 100 are positioned within the slider 102. FIG. 3 illustrates the second connector 98 positioned within the slider 102 and movable relative to the slider 102 against a biasing force of the biasing member 104. The third connector 100 is fixed in place relative to the slider 102. In at least one example, the slider 102 and third connector 100 may maintain a fixed position to secure the disconnect member 26 in place relative to the slider 102 while the second connector 98 with follower 106 and locking rod 28 may move proximally against the biasing force of the biasing member 104 relative to the slider 102 and disconnect member 26.

The first connector 96 may be pivotally mounted to the first lever 90 at the second pivot point 94. Advancing the first connector 96 advances the locking rod 28 relative to the disconnect member 26 and sleeve 30. The first actuator 22 may be configured to alternate pivot locations between the first and second pivot points 92, 94. For example, referring to FIGS. 4A and 5A, when moving the first lever 90 in a forward direction, the first lever 90 rotates about the second pivot point 94 while the second pivot point 94 maintains a position adjacent to the first stop member 84 of the handle 18. After returning to the rest position shown in FIG. 6A, the first lever 90 may pivot about the first pivot point 92 when the first lever 90 is moved proximally (e.g., rotated in the proximal direction) because the second pivot point 94 is not constrained against the first stop member 84. The first connector 96 maintains a fixed axial position when the first lever 90 rotates in a forward or distal direction, and the first connector 96 moves axially (e.g., in the distal direction) when the first lever 90 rotates in a rearward or proximal direction as shown in FIG. 7A.

When the first lever 90 rotates in the rearward or proximal direction as shown in FIG. 7A, the slider 102 is restricted in rearward or proximal movement by contact with the second stop member 86, which forces pivotal motion of the first lever 90 about the first pivot point 92. Rotational movement of the first lever in the forward or distal direction as shown in FIG. 5A creates pivotal movement about the second pivot point 94, thereby moving the slider 102 along the track 88 in the distal or forward direction to advance the disconnect member 26 and sleeve 30.

The second actuator 24 includes a second lever 110, an aperture 112, and a cam surface 114. The second lever 110 extends through the second actuator slot 82. The proximal end 62 of the carrier member is secured to the second actuator 24 within the aperture 112, and the locking rod 28 passes through the aperture 112. The cam surface 114 defines an interface surface between the second actuator 24 and the follower 106. When the follower 106 contacts the cam surface 114 when the follower is advanced in a forward direction, the follower 106 forces the second lever 110 to rotate into a rotated position shown in FIG. 5A. The cam surface 114 is constructed to translate the linear force applied by the follower 106 into a rotational force that rotates the second lever 110. The follower 106 may include a rounded tip that promotes lower friction contact between the follower 106 and the cam surface 114.

The disconnect member 26 includes a wire member 120 and a rod member 122, which are connected together. The wire member 120 defines a distal end 124 of the disconnect member 26, and the rod member 122 defines a proximal end 126 of the disconnect member 26. The distal end 124 is releasably connected to the retention protrusion 54 (see FIGS. 9A-B). The proximal end 126 is connected to the third connector 100 (see FIG. 3).

The locking rod 28 includes first (distal) and second (proximal) ends 128, 130 (see FIG. 2A). The first end 128 is arranged adjacent to the second locking member 42, and may be arranged to abut against the proximal end 58 of the second locking member. The second end 130 is connected to the first connector 96 (see FIG. 3). The locking rod 28 is movable relative to the sleeve 30 (which is positioned internal the locking rod 28) and cutting device 16 (within which the locking rod 28 is positioned).

The sleeve 30 includes first (distal) and second (proximal) ends 132, 134 (see FIG. 2A). The first end 132 is arranged to overlap the retention protrusion 54 as shown in FIG. 9A. The second end 134 is connected to the second connector 98 (see FIG. 3). The sleeve 30 is movable relative to the disconnect member 26 (which is positioned internal the sleeve 30) and the locking rod 28 (within which the sleeve 30 is positioned).

Referring now to FIGS. 4A-9B, operation of the suture locking device 10 will be described in further detail. The suture locking device 10 may be operated to lock a suture 34 for the purpose of, for example, holding closed a puncture 6 in a vessel wall 4. The suture 34 may include first and second suture ends 33, 35 that extend through suture openings 8 on opposing sides of the puncture 6. The suture 34 may extend across the puncture 6 on an internal side of the vessel wall 4 as shown in FIG. 4B. The puncture 6 may be held closed by applying or maintaining tension in the first and second suture ends 33, 35 using, for example, the locking assembly 12.

The suture locking device 10 may begin in a rest state or rest position as shown in FIGS. 4A-C. In the rest state, the locking assembly 12 is retracted within the carrier member 14. The first and second locking members 40, 42 are separated axially so that the latch recess 46 is exposed or uncovered relative to the second locking member 42. The latch recess 46 is covered by or unexposed at a position within the carrier member 14.

Referring now to FIGS. 5A-C, the suture locking device 10 is moved into a loading state or position by advancing the first lever 90 in a forward or distal direction. The suture locking device 10 is moved into the loading state by advancing the first lever 90 in a forward or distal direction. Advancing the first lever 90 pivots the first lever 90 about the second pivot point 94. Pivoting about the second pivot point 94 advances the slider 102 along track 88, which advances the disconnect member 26 and sleeve 30 relative to the locking rod 28, cutting device 16 and carrier member 14. The first end 128 of the sleeve 30 pushes against a proximal surface 45 of the first locking member 40 to advance the first locking member 40 out of the distal opening 64 of the carrier member 14. In this advanced position, the latch recess 46 is exposed outside of the carrier member 14. The operator may then route the first and second suture ends 33, 35 into the latch recess 46 through the opening 48 and into the distal and/or proximal portions 50, 52 of the latch recess 46. Typically, positioning the suture 34 within the latch recess 46 is performed outside of the patient spaced away from the vessel 2.

While maintaining some tension in the suture 34, the operator then retracts the first lever 90 back into the rest position as shown in FIGS. 6A-C. Pivoting the first lever 90 about the second pivot point 94 into the rest position shown in FIG. 6A loads the suture 34 into the carrier member 14. The suture 34 is positioned within the suture opening 66 of the carrier member 14 and the suture slot 78 of the cutting device 16. The first and second locking members 40, 42 are maintained spaced apart axially while in the loaded or captured state, as shown in FIGS. 6A-C.

Moving the first lever 90 into the rest position from the advanced position as shown in FIGS. 6A-C pulls the first locking member 40 proximally via the connection of the disconnect member 26 at the retention protrusion 54 of the first locking member 40 and the connection of the disconnect member 26 to the slider 102. The sleeve 30 remains in an overlapping position relative to the distal end 124 of the disconnect member 26 and the retention protrusion 54 to maintain connection of the disconnect member 26 to the first locking member 40.

In the loaded position shown in FIGS. 6A-C, the suture 34 may slide relative to the locking assembly 12, carrier member 14 and cutting device 16 (e.g., in a lateral direction through the suture locking device 10). While maintaining some tension in the suture 34, the operator may advance the suture locking device 10 along the suture 34 toward the puncture 6. In some arrangements, the puncture 6 is hidden from the operator's view and is accessible only through a percutaneous incision through a skin layer of the patient. The operator may insert the distal end of the suture locking device (i.e., the locking assembly 12 and distal end 60 of the carrier member 14) through the percutaneous incision so that the distal end of the suture locking device 10 is hidden from view. The operator advances the suture locking device 10 until resistance is felt due to contact of the distal end of the suture locking device 10 with the vessel 2. Typically, the operator maintains tension in the suture 34 that holds closed the puncture 6 to limit the chance of passing the suture locking device 10 through the puncture 6.

With the suture locking device 10 positioned adjacent to the puncture 6 on an exterior of the vessel wall 4, the operator actuates the first lever 90 in a rearward or proximal direction as shown in FIGS. 7A-C to lock the locking assembly 12. Actuating the first lever 90 in a rearward direction from the rest state shown in FIGS. 6A-C pivots the first lever 90 about the first pivot point 92. Pivoting the first lever 90 about the first pivot point 92 holds the slider 102 in a fixed axial position against the second stop member 86 within the handle 18 and advances the first connector 96. This actuation advances the locking rod 28 relative to the disconnect member 26, the sleeve 30, the carrier member 14 and the cutting device 16. Advancing the locking rod 28 contacts the distal end 124 of the locking rod 28 against the proximal end 58 of the second locking member 42 to advance the second locking member 42 distally relative to the first locking member 40.

The suture 34 may move within the locking recess 56 of the second locking member 42 as the second locking member 42 advances distally until the suture 34 is captured between surfaces of the locking recesses 56 and surfaces of the distal portion 50 of the latch recess 46. In this advanced position for the second locking member 42, the locking assembly 12 may be considered to be in a locked state or locked position. This locked state or locked position for the locking assembly 12 may be maintained using, for example, an interference fit, a snap fit, or other connection between the first and second locking members 40, 42 that limits disconnection of the first locking member 40 from the second locking member 42. The suture 34 may be locked or connected to the locking assembly 12 when the locking assembly 12 is in the locked state. Tension in the suture 34 may be maintained when locked to the locking assembly 12. This tension in the suture 34 may help maintain closed the puncture 6 to assist in maintaining hemostasis and reducing blood flow through the puncture 6.

After locking the locking assembly 12, the operator may cut the suture 34 by operating the second actuator 24. The operator may move the second lever 110 in a lateral direction such as by rotating the second lever 110 about a longitudinal axis X of the suture locking device 10. Rotating the second lever 110 rotates the cutting device 16 relative to the carrier member 14. Rotation of the cutting device 16 with the suture 34 positioned within the suture opening 66 of the carrier member 14 and suture slot 78 of the cutting device 16 captures the suture 34 against the cutting surface 76 to cut the suture 34.

Holding the first lever 90 in the rearward or proximal rotated position as shown in FIGS. 7A-7C while actuating the second lever 110 causes the cam surface 114 of the second actuator 24 to contact the follower 106 of the first actuator 22. This contact between the follower 106 and cam surface 114 moves the follower 106 in a rearward or proximal direction relative to the first lever 90 and slider 102. Moving the follower 106 in a rearward direction while the slider 102 is held against the third connector 100 forces the second connector 98 in the rearward direction against biasing forces of the biasing member 104.

The sleeve 30 is connected to the second connector 98 as described above so that rearward movement of the second connector 98 retracts the sleeve 30 in a rearward or proximal direction relative to the disconnect member 26 as shown in a comparison of FIGS. 9A and 9B. With the sleeve 30 retracted from off of the distal end 124 of the disconnect member 26 and off of the retention protrusion 54 of the first locking member 40, the disconnect member (e.g., the wire 120) may disconnect from the retention protrusion 54. With the first locking member 40 disconnected from the disconnect member 26, the locking assembly 12 may be released from the suture locking device 10 so that the locking assembly 12 is deposited within the percutaneous incision adjacent to the puncture 6 while the remaining portions of the suture locking device 10 are removed from the patient.

Operation of the second actuator 24 (e.g., by rotating the second lever 110 about the longitudinal axis X) may cut the suture 34 and may disconnect the locking assembly 12 from the suture locking device 10. Operation of the actuator assembly 20 may cut the suture 34 within the carrier member 14 and within a percutaneous incision without visual inspection by the operator of the point of cutting and/or locking of the suture 34.

Referring now to FIGS. 10-18B, another example suture locking device 200 is shown and described. The suture locking device 200 includes a locking assembly 212, a carrier member 214, a cutting device 216, a handle 218, an actuator assembly 220, a disconnect member 226, a locking rod 228, and a suture path defined through a portion of the suture locking device 200. The suture locking device 200 may perform a similar function as the suture locking device 10 described above to lock a suture 34 with the locking assembly 212 and cut the suture 34 with the cutting device 216. The suture locking device 200 may operate to expose the locking assembly 212 by retracting the carrier member 214 rather than by extending the locking assembly distally relative to the carrier member 214, as is the operation of the suture locking device 10.

Figure 11:
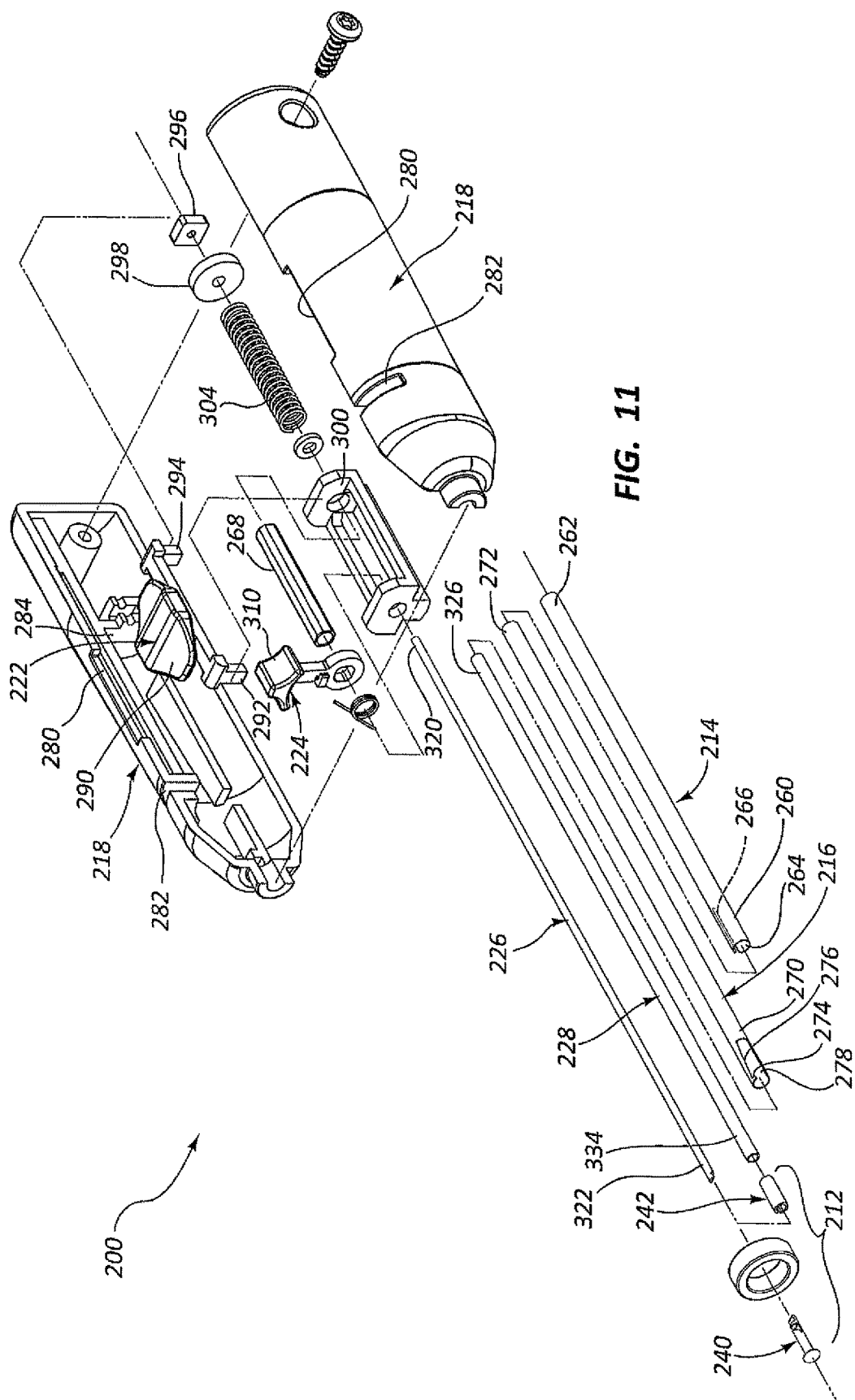
FIG. 11 is an exploded perspective view of the suture locking device of FIG. 10.
Figure 12:
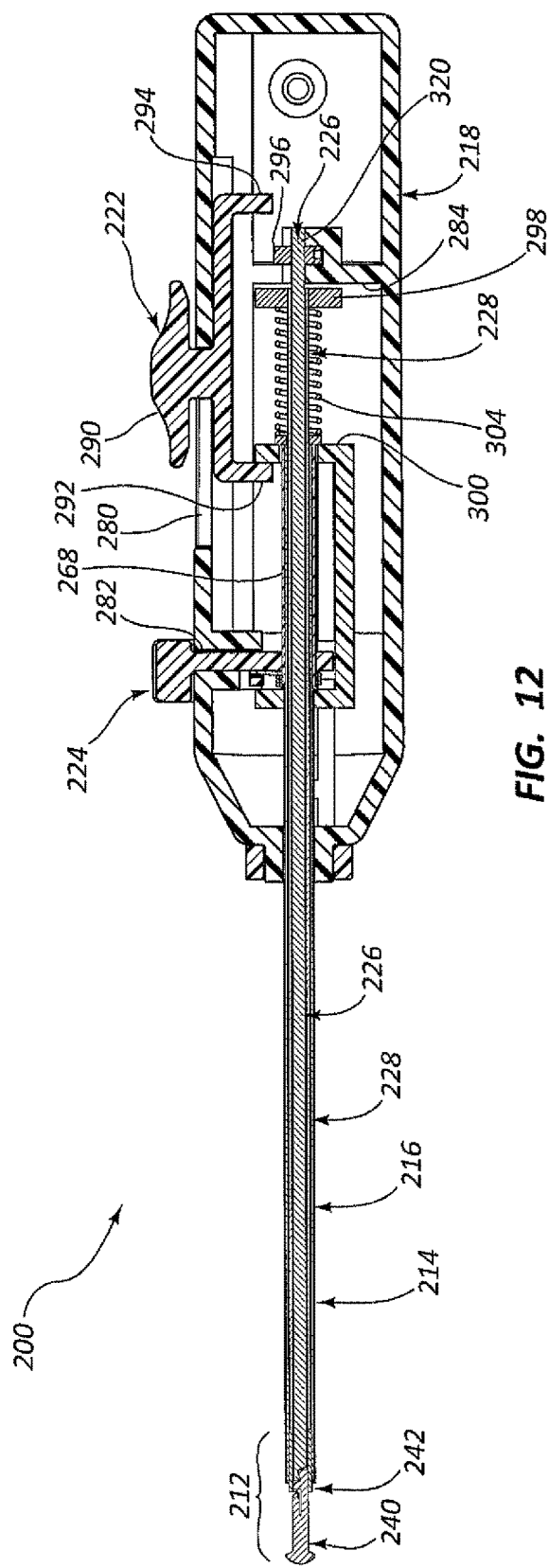
FIG. 12 is a cross-sectional view of the suture locking device of FIG. 10 taken along cross-section indicators 12-12.

The locking assembly 212 includes first and second locking members 240, 242 as shown with reference to at least FIGS. 11 and 12. The first locking member 240 includes a distal surface 244, a latch recess 246 having a latch opening 248 and a distal latch portion 250, and a retention protrusion 254 at a proximal end thereof (see FIG. 13C). The second locking member 242 includes a locking recess 256 at a distal end thereof, and a proximal end 258 (see FIG. 17D). The latch recess 246 is sized to receive the suture 34 therein when the locking assembly 212 is exposed outside of the carrier member 214. The locking assembly 212 is configured to lock the suture 34 relative to the locking assembly 212 by advancing the second locking member 242 relative to the first locking member 240 to capture the suture 34 within the distal portion 250 of the latch recess 246. The second locking member 242 may advance distally relative to the first locking member 240 until the retention protrusion 254 is exposed proximal of the proximal end 258 of the second locking member 242. When the retention protrusion 254 is exposed outside of the second locking member 242, the first locking member 240 may disconnect from the disconnect member 226 thereby releasing the locking assembly 212 from the suture locking device 200.

The carrier member 214 includes distal and proximal ends 260, 262, a distal opening 264 within which the locking assembly 212 may be positioned, and a suture opening 266. The carrier member 214 is mounted at its proximal end 262 to the handle 218. The carrier member 214 may be adjustably mounted within the handle 218 to provide some relative axial movement between the carrier member 214 and the handle 218. The locking assembly 212 is adjustably mounted within the distal opening 264 at the distal end 260. Moving the locking assembly 212 between various axial positions relative to the carrier member 214 provides loading, loaded, locked, and cutting states or positions of the suture locking device 200 as will be described below in further detail with respect to FIGS. 13-18B.

The suture openings 266 may be positioned along sidewalls of the carrier member 214 adjacent to the distal end 260. The suture openings 266 may provide at least a portion of a suture pathway through which the suture 34 may extend when the locking assembly 212 is moved into the loaded state and later in the locked state or position in which the suture is arranged for cutting by the cutting device 216.

The suture locking device 200 may also include a spacer 268 positioned within the handle 218 in alignment with the carrier member 214 and a portion of the actuator assembly 220. The spacer 268 may be used to advance the carrier member 214 under forces applied by the biasing member 304 after the carrier member 214 has been retracted into the position shown in FIG. 12.

The cutting device 216 includes distal and proximal ends 270, 272, a tab 274 defining a cutting surface 276, and a suture slot 278 through which the suture 34 extends prior to cutting of the suture 34, The construction and operation of the cutting device 216 may have similarities to the cutting device 16 described above. Typically, the suture 34 passes through the suture slot 278 and the suture openings 266 of a carrier member 214. Relative rotation between the cutting device 216 and carrier member 214 captures the suture 34 between an edge surface of the cutting opening 266 and the cutting surface 276 to pinch and sever the suture 34. Typically, the suture 34 is cut within the carrier member 214.

The cutting device 216 may be retained interior of the carrier member 214. A portion of the actuator assembly 220 may contact the cutting device 216 to provide relative rotation between the cutting device 216 and the carrier member 214. In one example, the proximal end 272 of the cutting device 216 is mounted to a mounting device or connector within the handle 218.

The handle 218 includes first and second actuator slots 280, 282 sized to receive first and second actuators 222, 224 of the actuator assembly 220. Typically, the first actuator slot 280 is arranged longitudinally along a length direction to provide longitudinal or axial movement of the first actuator 222 relative to the handle 218. The second actuator slot 282 may be opened around a periphery or in a lateral direction across a portion of the handle 218 to provide some relative lateral or rotational motion of the second actuator 224 about a longitudinal axis of the handle 218.

The handle 218 may further include a first stop member 284 that provides a support surface or base with which features of the actuator assembly 220 contact in order to provide actuating motion or operation within the handle 218. In one example, the first stop member 284 acts as a biasing member support surface against which one end of a biasing member of the actuator assembly 220 operates, while an opposing side of the first stop member 284 acts as a position stop for a connector of the actuator assembly 220.

The first actuator 222 of the actuator assembly 220 includes a first lever 290, first and second contact members 292, 294, first, second and third connectors 296, 298, 300, and a biasing member 304. The first lever 290 is positioned within the first actuator slot 280 of handle 218. The first and second contact members 292, 294 are connected to the first lever 290 so that axial movement of the first lever 290 moves the first and second contact members 292, 294 in the axial direction. In some arrangements, the first and second contact members 292, 294 are connected in an axially spaced apart arrangement with a fixed axial spacing therebetween. In some arrangements, movement of the first lever 290 in a first axial direction causes the lever 290 to contact the first contact member to operate the carrier member 214. Movement of the first lever 290 in an opposite axial direction provides operation of, for example, the locking rod 228. The biasing member 304 may bias the first lever 290 into a rest position to resist unintended actuation of the first lever 290 in a particular direction.

The disconnect member 226 is mounted at its proximal end 320 to the first connector 296. The first connector 296 may maintain a fixed axial position relative to the handle 218, for example, by connection to the first stop member 284 (see FIG. 12). The locking rod 228 may be mounted at its proximal end 326 to the second connector 298. The second connector 298 may be axially movable within the handle 218. A second connector 298 may have a proximal position stop defined by the first stop member 284 or other feature within the handle 218. The second contact member 294 may contact the second connector 298 to advance the second connector 298 and locking rod 228 relative to the disconnect member 226.

The carrier member 214 may be connected at its proximal end 262 to the third connector 300. The third connector 300 may also be axially movable or adjustable within the handle 218. The third connector 300 may be biased in a forward or distal direction with the biasing member 304. When biased in the forward direction, the carrier member 214 covers the latch recess 246 of the locking assembly 212. A third connector 300 may be adjustable into a rearward or retracted position by operating the first lever 290 in a rearward axial direction and contacting the first contact member 292 against the third connector 300. Retracting the carrier member 214 exposes the latch recess 246 so that the suture 34 may be positioned within the latch recess 246.

The first lever 290 may be operated between three distinct positions within the first actuator slot 280. In a first or rest position shown in FIGS. 13A-C, the carrier member 214 is biased in a forward direction covering the latch recess 246. The first lever 290 is positioned at some location spaced between proximal most and distal most positions within the first actuator slot 280. The first lever 290 may be operated into a retracted position shown in FIGS. 14A-C in which the first contact member 292 retracts the carrier member 214 to expose the latch recess 246. The first lever 290 may be operated into an advanced or distal position as shown in FIGS. 15A-C in which the second contact member 294 advances the locking rod 228 in a forward or distal direction to move the second locking member 242 distally relative to the first locking member 240. In this advanced position, the first lever 290 operates to lock the locking assembly 212 to lock the suture 34 relative to the locking assembly 212. Also in this advanced position, the first lever 290 operates the second locking member 242 to expose the retention protrusion 254 of the first locking member 240 and permit disconnection of the locking assembly 212 from the disconnect member 226. Typically, the second actuator 224 is operated at this point to sever the suture 34 so that the locking assembly 212 and suture 34 may be detached from the suture locking device 200.

The second actuator 224 includes a second lever 310 positioned within the second actuator slot 282. The second lever 310 may pivot through the second actuator slot 282. In one example, the second lever 310 pivots about a pivot axis defined by a longitudinal axis extending through the carrier member 214. A portion of the second lever 310 may extend into contact with the cutting device 216. Lateral or rotational movement of the second lever 310 rotates the cutting device 216 relative to the carrier member 214.

Referring to FIGS. 16A-C and 17A-C, rotation of the cutting device 216 by operation of the second lever 310 of the second actuator 224 may cut the suture 34.

Referring to FIGS. 18A-B, a locking assembly 212 may be disconnected from the disconnect member 226 by advancing the second locking member 242 distally to uncover the retention protrusion 254 and a distal end 322 of the disconnect member 226. The retention protrusion 254 and distal end 322 may have mating latch or other connection features such as, for example, mating wedge, T-shaped, lip, or track features, which when moved radially relative to each other permits disconnection. By advancing the second locking member 242 distally to expose the retention protrusion 254 and distal end 322, and removing the second locking member 242 from within the space radially adjacent to the retention protrusion 254 and distal end 322, there is sufficient space within the cutting device 216 to permit relative radial movement between the retention protrusion 254 and distal end 322. Inherent spring or cantilever forces present in the disconnect member 226 near the distal end 322 may promote this relative radial movement to permit disconnection. Disconnection between the retention protrusion 254 and distal end 322 of the disconnect member 226 may be accelerated by applying a proximally directed force or retraction force to the handle 218 after the locking assembly 212 is locked to the suture 34.

Referring now to FIGS. 13A-17C, an example method of operation for the suture locking device 200 to close a puncture 6 in a vessel wall 4 is described in further detail. Referring to FIGS. 13A-C, first and second suture ends 33, 35 of the suture 34 extend through suture openings 8 on opposing sides of the puncture 6 and are accessible outside of the patient (e.g., outside of a percutaneous incision that provides access to the puncture 6). The suture locking device 200 is in a rest position with the locking assembly 212 positioned within the carrier member 214.

Figure 14C:
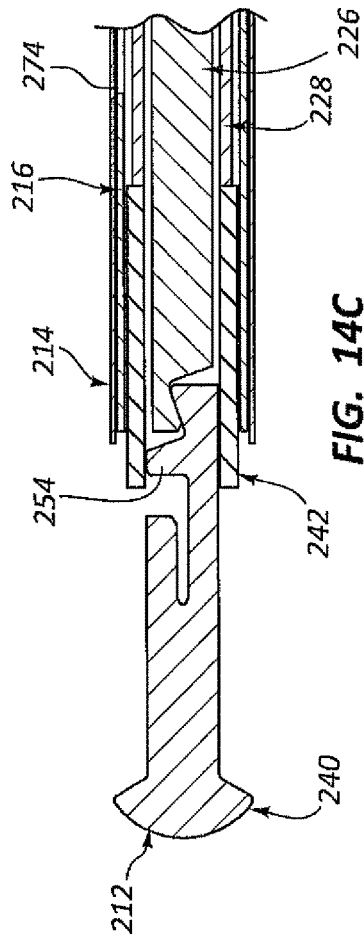
FIGS. 14A-C illustrate the suture locking device of FIG. 10 in a loading state.
Figure 14A:
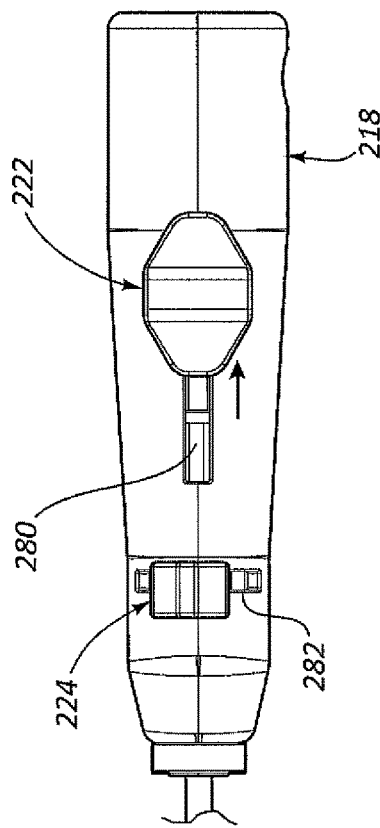
Figure 14B:
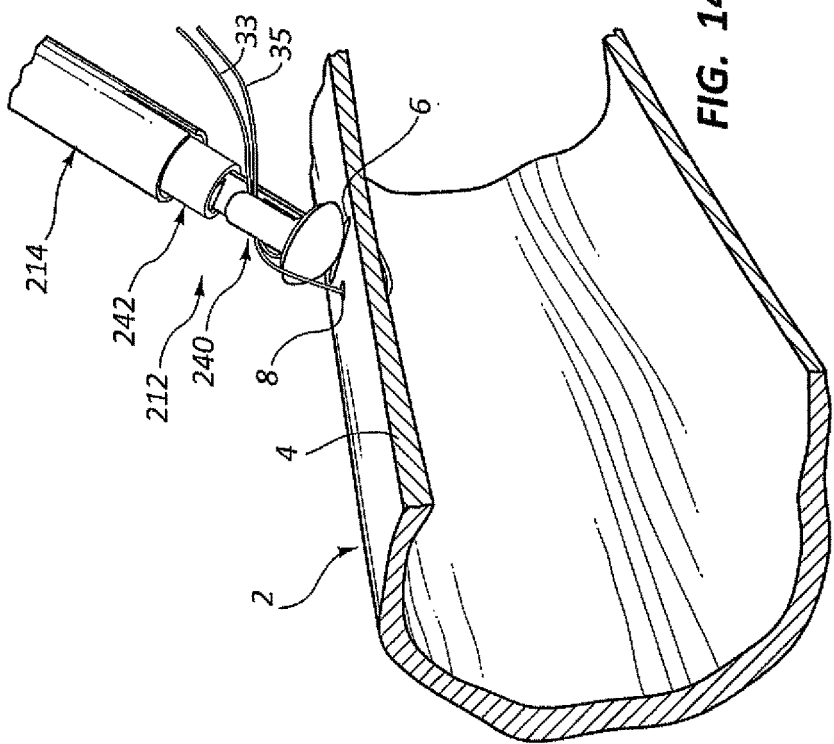
Figure 17D:
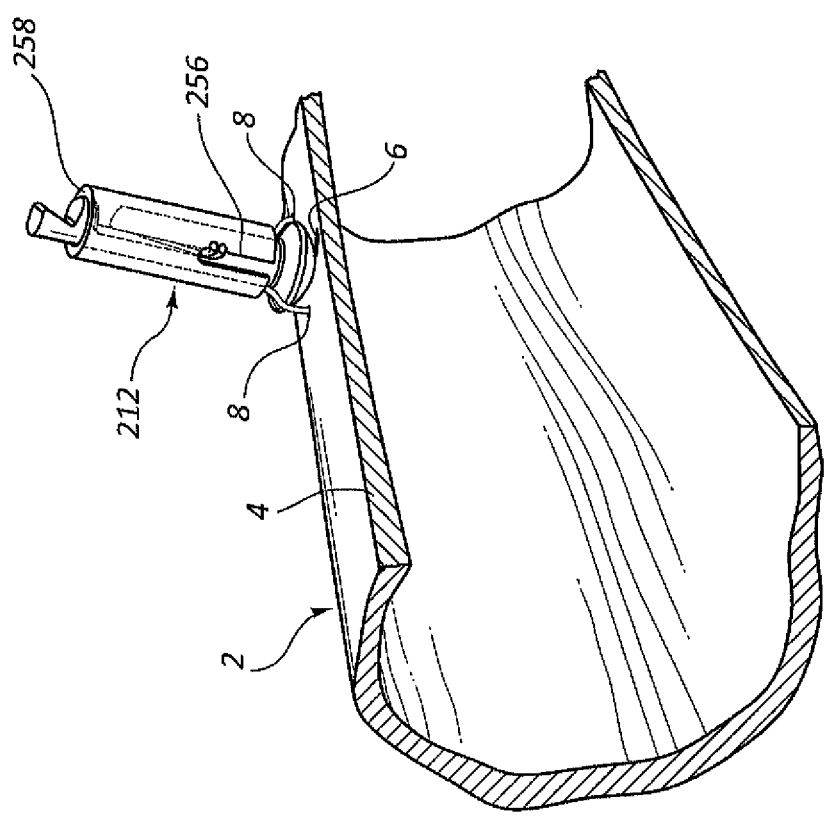
FIG. 17D illustrates the suture locking device of FIG. 10 in a deployed state.

Referring to FIGS. 14A-C, the operator actuates the actuator assembly 220 to expose the locking assembly 212 by retracting the first lever 290 in a proximal direction to withdraw the carrier member 214. The operator may place or thread the suture ends 33, 35 within the latch recess 246.

While applying some tension in the suture, the operator releases the first lever 290 so that the first lever 290 moves back to the rest position under the biasing force of biasing member 304. The suture 34 is drawn into the carrier member 214 as shown in FIGS. 15A-C. The suture 34 moves into the suture openings 266. The locking assembly 212 remains unlocked to permit the suture 34 to pass through the locking assembly 212 freely in a generally lateral direction.

Referring to FIGS. 15A-C, while applying some tension to the suture 34, the operator may slide the suture locking device 200 along the suture 34 to a position adjacent the puncture 6. In some arrangements, advancing the suture locking device 200 along the suture 34 buries a distal end of the suture locking device 200 within a percutaneous incision and out of view of the operator (sometimes referred to as a blind placement wherein the operator continues to operate the suture locking device 200 based on tension and feel). Typically, the operator advances the suture locking device 200 until pressure is felt as a result of contacting the locking assembly 212 against the vessel wall 4 at the puncture 6. Application of tension to the suture 34 may help maintain closure of the puncture 6 and resist advancing the suture locking device 200 through the puncture 6 and into the vessel 2.

Referring to FIGS. 16A-C, the operator advances the first lever 290 into the forward position thereby advancing the locking rod 228 to contact the distal end 334 of the locking rod 228 against the proximal end 258 of the second locking member 242. The second locking member 242 captures the suture 34 within the distal portion 250 of the latch recess 246 to lock a position of the suture 34 relative to the locking assembly 212. The first and second locking members 240, 242 may include features that promote permanent connection therebetween when the second locking member 242 is moved into the advanced or locked position. In some arrangements, the locked position or orientation of the locking assembly 212 may be maintained with, for example, an interference fit, a snap fit, or other bond or connection that limits movement of the second locking member 242 proximally relative to the first locking member 240 (i.e., disconnecting of the locking assembly 212).

As described above, advancing the second locking member 242 into the locked position also exposes the retention protrusion 254 and distal end 322 of the disconnect member 226 thereby providing a disconnection of the locking assembly 212 from the suture locking device 200. By continuing to apply tension in the suture 34, the locking assembly 212 remains positioned within the carrier member 214 until the suture 34 is cut to permit physical separation of the locking assembly 212 from the suture locking device 200.

The suture 34 is cut by operating the second actuator 224 to rotate the second lever 310 and to rotate the cutting device 216 relative to the carrier member 214. The suture 34 is captured between the suture opening 266 and the cutting surface 276 of the cutting device 216. The operator then removes the suture locking device 200 leaving behind the locking assembly 212 locked or permanently secured to the suture 34. Typically, at least some tension is maintained in the suture 34 upon locking the locking assembly 212 to maintain closure of the puncture 6 thereby improving hemostasis and reducing blood flow from the puncture 6.

FIGS. 19 and 20 illustrate another example cutting arrangement that includes a carrier member 414 and a cutting device 416, wherein the carrier member 414 includes a suture outlet opening 466 and cutting device 416 includes a cutting surface 474. A suture 434 passes through the suture outlet opening 466. Relative rotation between the carrier member 414 and cutting device 416 captures and cuts of the suture 434.

Figure 21:
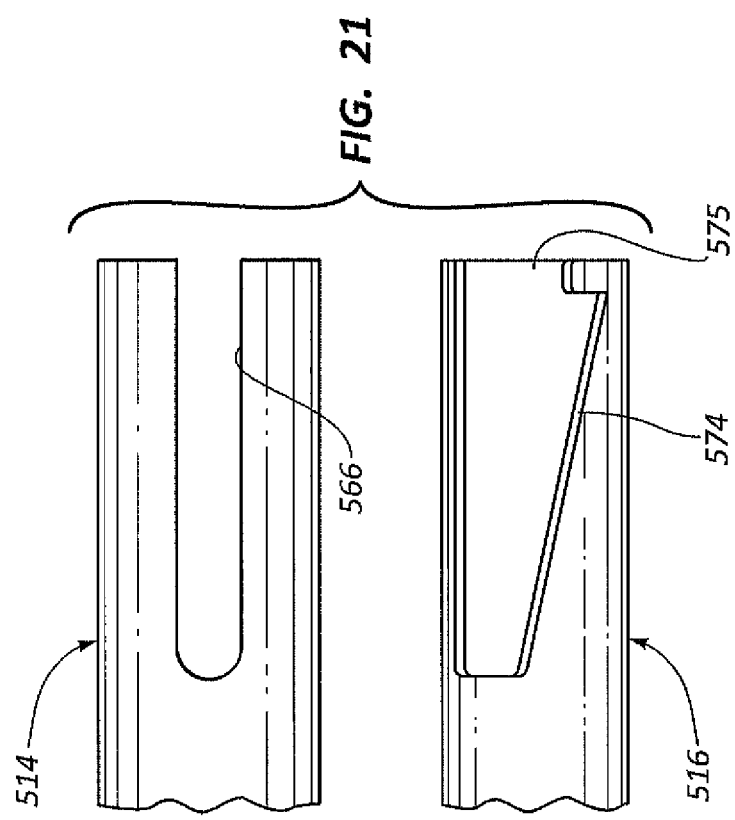
FIG. 21 is a side view of another example cutting arrangement according to the present disclosure.
Figure 22:
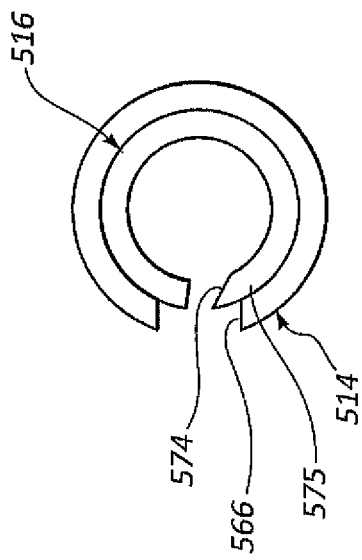
FIG. 22 is an end view of the cutting arrangement shown in FIG. 21 assembled together.

FIGS. 21 and 22 illustrate another cutting arrangement that includes a carrier member 514 and a cutting device 516. The carrier member 514 includes a suture outlet opening 566. The cutting device 516 includes a cutting surface 574. The cutting device 516 may include a pre-bend portion 575 that biases the cutting surface 574 radially outward toward the outlet opening 566. The cutting surface 574 may be arranged at a non-parallel angle relative to a longitudinal axis of the cutting device 516 to better capture the suture between the suture outlet opening 566 and the cutting surface 574 to promote cutting of the suture.

While this invention has been described with reference to certain specific embodiments and examples, it will be recognized by those skilled in the art that many variations are possible without departing from the scope and spirit of this invention. The invention, as defined by the claims, is intended to cover all changes and modifications of the invention which do not depart from the spirit of the invention. The words "including" and "having," as used in the specification, including the claims, shall have the same meaning as the word "comprising."

What is claimed is:

1. A suture locking device, comprising:
    a hollow carrier member having a slot formed in a sidewall thereof;
    a locking assembly mounted at a distal end of the carrier member, the locking assembly comprising:
        a first locking member having a latch portion, the latch portion comprising a latch recess having a lateral opening, a distal portion extending distal to the lateral opening, and a proximal portion extending proximal to the lateral opening;
        a second locking member connectable to the first locking member and movable relative to the first locking member;
    a suture path receptive of a suture and defined at least in part between the first and second locking members and at least in part within the slot of the carrier member;
    a cutter assembly;
    an actuator assembly operable to expose the latch portion for receipt of the suture, draw a portion of a suture into the carrier member along the suture path, move the first and second locking members together relative to each other to lock the suture between the first and second locking members with the suture extending laterally through the latch portion relative to a longitudinal axis of the first and second locking members when the first and second locking members are in a locked position, and rotate the cutter assembly to cut the suture within the carrier member, wherein the cutter assembly captures the suture between a suture opening and a cutting surface of the cutter assembly.

2. The suture locking device according to claim 1 wherein the latch portion has entrance and exit portions across a width of the first locking member, at least one of the entrance and exit portions being radially aligned with the slot in the carrier member.

3. The suture locking device according to claim 1 wherein the suture path exits through the sidewall of the carrier member.

4. The suture locking device according to claim 1 further comprising a handle positioned at a proximal end of the carrier member, the actuator assembly including a first actuator lever mounted to the handle and operable to move the first and second locking members relative to each other, and a second actuator lever mounted to the handle and configured to operate the cutter assembly.

5. The suture locking device according to claim 4 further comprising a disconnect member arranged to connect the locking assembly to the handle, wherein operating the second actuator lever disconnects the disconnect member from the locking assembly.

6. The suture locking device according to claim 5 further comprising a sleeve movable with the actuator assembly between a connect position covering a portion of the disconnect member to maintain connect of the disconnect member to the locking assembly, and a disconnect position wherein a portion of the disconnect member is exposed to permit disconnect of the disconnect member from the locking assembly.

7. The suture locking device according to claim 1 wherein the cutter assembly includes a cutting device positioned in the carrier member and movable across the slot to cut the suture.

8. The suture locking device according to claim 7 wherein the cutting device is operable by rotating relative to the carrier member.

9. The suture locking device according to claim 1 further comprising a locking rod coupled to the actuator assembly and operable to move the first and second locking members relative to each other to lock the suture.

10. A suture locking device configured to lock a suture, comprising:
a suture locking assembly comprising a first locking member and a second locking member, the first locking member having a latch portion;
a suture cutting member having a cutting surface extending parallel to a longitudinal axis of the suture cutting member;
an actuator assembly including a first actuator longitudinally operable in a first slot oriented in a first direction to lock the suture with the suture locking assembly by capturing the suture between the first and second locking members with the suture extending laterally through the latch portion relative to a longitudinal axis of the first and second locking members when the first and second locking members are in a locked position, and a second actuator laterally operable in a second slot oriented in a second direction to concurrently cut the suture with the suture cutting member and disconnect the suture locking assembly from the suture locking device, wherein the first direction is perpendicular to the second direction.

11. The suture locking device according to claim 10, wherein the suture locking assembly includes first and second locking members that define a suture path there between, wherein moving the first and second locking members relative to each other locks the suture relative to the suture locking assembly.

12. The suture locking device according to claim 10, further comprising a carrier member, the suture locking assembly being releasably mounted at a distal end of the carrier member.

13. The suture locking device according to claim 10, wherein the actuator assembly includes first and second levers, the first lever being coupled to the suture locking assembly, and the second lever being coupled to the suture cutting member.

14. A method of locking a suture across a vessel opening, comprising:
providing a suture locking device having a locking assembly, a carrier member, first and second actuators, and a cutting member, the locking assembly comprising a first locking member and a second locking member, the first locking member comprising a latch portion;
passing the suture through the locking assembly and through a sidewall of the carrier member;
operating the first actuator in a first slot oriented in a first direction to lock the locking assembly to the suture with the suture between the first and second locking members and extending laterally through the latch portion relative to a longitudinal axis of the first and second locking members when the first and second locking members are in a locked position;
operating the second actuator in a second slot oriented in a second direction to cut the suture with a cutting surface extending parallel to a longitudinal axis of the cutting member by rotation of the cutting member within the carrier member, the second direction being perpendicular to the first direction;
detaching the locking assembly from the suture locking device by operating one of the first or second actuators.

15. The method according to claim 14, wherein operating the second actuator to cut the suture with the cutting member includes rotating the cutting member relative to the carrier member.

16. The method according to claim 14, wherein cutting the suture and detaching the locking assembly includes rotating the second actuator about a longitudinal axis of the suture locking device.

17. The method according to claim 14, wherein the suture locking device further includes a handle mounted at a proximal end of the carrier member, and the first actuator includes a lever mounted to the handle, wherein operating the first actuator to lock the locking assembly includes moving the lever longitudinally relative to the handle, and operating the second actuator to cut the suture includes rotating the lever laterally relative to the handle.

18. The method according to claim 14, wherein the suture locking device includes a disconnect member coupled to the locking assembly at a distal end and coupled to one of the first and second actuators at a proximal end, wherein detaching the locking assembly from the suture locking device includes uncovering a portion of the locking assembly to permit disconnection of the disconnect member from the locking assembly.

19. A method of operating a suture locking device, comprising:
providing the suture locking device with a locking assembly, a carrier member having a suture opening or slot, an actuator assembly, and a cutting member, the locking assembly including first and second locking members and being mounted to the carrier member, the first and second locking members being movable relative to each other, the first locking member comprising a latch portion, the latch portion comprising a latch recess having a lateral opening, a distal portion extending distal to the lateral opening, and a proximal portion extending proximal to the lateral opening;

operating the actuator assembly to connect the first and second locking members in a locked position wherein a suture is captured between the first and second locking members and laterally through the latch portion relative to a longitudinal axis of the first and second locking members when the first and second locking members are in the locked position;

operating the actuator assembly to rotate the cutting member relative to the carrier member, wherein rotation of cutting member captures the suture between the suture opening or slot of the carrier member and a cutting surface of the cutting member;

disconnecting the locking assembly from the carrier member concurrently with operating the actuator assembly to connect the first and second locking members or operating the actuator assembly to move the cutting member relative to the carrier member.

20. The method according to claim 19, wherein the suture locking device includes a handle, and the actuator assembly includes first and second levers mounted to the handle, wherein operating the actuator assembly to connect the first and second locking members into the locked portion includes moving the first lever longitudinally relative to the handle, and operating the actuator assembly to rotate the cutting member includes rotating the second lever relative to the handle.

21. The method according to claim 19, further comprising passing the suture laterally through the locking assembly prior to operating the actuator assembly to connect the first and second locking members in the locked position.

* * * * *